(12) United States Patent
Hecht et al.

(10) Patent No.: US 6,500,636 B1
(45) Date of Patent: Dec. 31, 2002

(54) CHIMERIC PRE-ACTIVATED TRANSCRIPTION FACTORS

(75) Inventors: Peter Hecht, Newton, MA (US); Kevin T. Madden, Boston, MA (US); Gerald R. Fink, Chestnut Hill, MA (US)

(73) Assignees: Microbia, Inc., Cambridge, MA (US); Whitehead Institute for Biomedical Research, Cambridge, MA (US)

( * ) Notice: Subject to any disclaimer, the term of this patent is extended or adjusted under 35 U.S.C. 154(b) by 0 days.

(21) Appl. No.: 09/196,270

(22) Filed: Nov. 19, 1998

Related U.S. Application Data

(60) Provisional application No. 60/066,129, filed on Nov. 19, 1997, provisional application No. 60/066,308, filed on Nov. 21, 1997, and provisional application No. 60/066,462, filed on Nov. 24, 1997.

(51) Int. Cl.$^7$ ................................................ C12P 21/06
(52) U.S. Cl. ................ 435/69.1; 435/320.1; 435/254.1; 536/23.4; 536/23.74
(58) Field of Search .............................. 435/69.1, 252.3, 435/254.1, 254.11, 320.1, 69.7, 69.9, 71.1, 71.3; 530/250, 371; 536/23.4, 23.7, 23.74, 23.72

(56) References Cited

U.S. PATENT DOCUMENTS

| | | | |
|---|---|---|---|
| 5,462,862 A | 10/1995 | Groenen et al. | ........... 435/69.1 |
| 5,589,362 A | 12/1996 | Bujard et al. | ............... 435/69.1 |
| 6,015,709 A | 1/2000 | Natsan | ....................... 435/366 |

OTHER PUBLICATIONS

Tilburn et al. (1995) EMBO Journal, 14/4:779–790.*
Orejas et al. (1995) Genes and Development, 9:1622–1632.*
Wang et al. (1997) Gene Therapy, 4:432–441.*
Gerber et al., "Transcriptional Activation Modulated By Homopolymeric Glutamine And Proline Stretches," *Science* 263:808–811 (1994).
Hao et al., "Mutation Of Phosphoserine 389 Affects p53 Function in Vivo," *The Journal of Biological Chemistry* 271(46):29380–29385 (1996).
Tilburn et al., "The Aspergillus PacC Zinc Finger Transcription Factor Mediates Regulation Of Both Acid– And Alkaline– Expressed Genes By Ambient pH," *The EMBO Journal* 14(4):779–790 (1995).
O'Reilly et al., "A Single Serine Residue At Position 375 Of VP16 Is Critical For Complex Assembly With Oct–1 and HCF and Is A Target Of Phosphorylation By Casein Kinase II," *The EMBO Journal* 16(9):2420–2430 (1997).
Wang et al., "Positive And Negative Regulation Of Gene Expression In Eukaryotic Cells With An Inducible Transcriptional Regulator," *Gene Therapy* 4:432–441 (1997).
Brakhage et la., "Use of reporter genes to identify recessive tans–acting mutations specifically involved in the regulation of *Aspergillus nidulans* penicillin biosynthesis genes," *J. Bacteriol.* 177:2781–2788 (1995).

Brakhage, "Molecular regulation of penicillin biosynthesis in *Apergillu* (*Emericella*) *nidulans*" *FEMS Microbiol Lett.* 148:1–10 (1997).
Chinenov et al., "Identification of redox–sensitive cysteines in GA–binding protein–alpha that regulate DNA binding and heterodimerization," *J. Biol. Chem.* 273:6203–6209 (1998).
Courey et al., "Analysis of Sp1 in vivo reveals multiple transcriptional domains, including a novel glutamine–rich activation motif," *Cell* 55:887–898 (1988).
Cress et al., "Critical structural elements of the VP16 transcriptional activation domain," *Science* 251:87–90 (1991).
Espeso and Penalva, "Three binding sites for the *Aspergilllus nidulans* PacC zinc–finger transcription factor are necessary and sufficient for regulation by ambient pH of the isopenicillin N aynthase gene promoter," *J. Biol. Chem.* 271:28825–28830 (1996).
Fischer et al., "GAL4 activates transcription in Drosophila," *Nature* 332:853–856 (1988).
Gu et al., "Activation of p53 sequence–specific DNA binding by acetylation of the p53 C–terminal domain," *Cell* 90:595–606 (1997).
Hope et al., "Structural and functional characterization of the short acidic transcriptional activation region of yeast GCN4 protein," *Nature* 333:635–640 (1988).
Hunter et al., "The regulation of transcription by phosphorylation," *Cell* 70:375–387 (1992).
Lambert et al., "Genetic analysis of regulatory mutants affecting synthesis of extracellular proteinases in the yeast *Yarrowia lipolytica*: Identification of RIM101/pacC homolog," *Mol. Cell. Biol.,* 17:3966–3976 (1997).
Li and Mitchell, "Proteolytic activation of Rim1p, a positive regulator of yeast sporulation and invasive growth" *Genetics* 145:63–73 (1997).
MacCabe et al., "Identification, cloning and analysis of the *Aspergillus niger* gene pacC, a wide domain regulatory gene responsive to ambient pH," *Mol. Gen. Genet.* 250:367–374 (1996).
Maccheroni et al., "The sequence of palF, an environmental pH response gene in *Aspergillus nidulans*," *Gene* 194:163–167 (1997).
mermod et al., "The proline–rich transcriptional activator of CTF/NF–I is distinct from the replication and DNA binding domain," *Cell* 55:887–878 (1988).

(List continued on next page.)

Primary Examiner—Karen Cochrane Carlson
(74) Attorney, Agent, or Firm—Fish & Richardson, P.C.

(57) ABSTRACT

Disclosed herein is a chimeric protein comprising a pre-activated transcription factor and a strong transcription activation domain for regulating fungal gene expression, and reagents and methods for constructing and using said protein.

54 Claims, 4 Drawing Sheets

OTHER PUBLICATIONS

Negrete–Urtasun et al., "Characterization of the pH signal transduction pathway gene palA of *Aspergillus nidulans* and identification of possible homologs," *J. Bacteriol.,* 179:1832–1835 (1997).

Orejas et al., "Activation of the Aspergillus PacC transcription factor in response to alkaline ambient pH requires proteolysis of the carboxy–terminal moiety," *Genes Dev.* 13:1622–1632 (19950.

Ostling et al., "Functional domains in the Mig1 repressor," *Mol. Cell Biol.* 16:753–761 (1996).

Pahl et al., "Control of gene expression by proteolysis," *Curr. Opin. Cell. Biol.* 8:340–347 (1996).

Sakashita et al., "Sequence–specific DNA recognition of the *Escherichia coli* Ada protein associated with the methylation–dependent functional switch for transcriptional regulation," *J. Biochem.*118:1184–1191 (1995).

Suarex et al., "Characterization of a Penicillium chrysogenum gene encoding a PacC transcription factor and its binding sites in the divergent pcbAB–pbcC promoter of the penicillin biosynthetic cluster," *Mol. Microbiol.* 20:529–540 (1996).

Su et al., "Molecular characterization of the yeast meiotic regulatory gene RIM1," *Nucleic Acids Res.* 21: 3789–3797 (1993).

Tanaka et al., "The Oct–2 gluamine–rich and proline–rich activation domains can synergize with each other or duplicates of themselves to activate transcription," *Mol. Cell Biol.* 14:6046–6055 (1994).

Tanaka et al., "Reconstitution of transcriptional activation domains by reiteration of short peptide segments reveals the modular organization of a glutamine–rich activation domain," *Mol. Cell. Biol.* 14:6056–6067 (1994).

Tanese et al., "Coactivators for a proline–rich activator purified from teh multisubunit human TFID complex," *Genes Dev.* 5:2212–2224 (1991).

Then Bergh et al., "Regulation of the *Aspergillus nidulans* penicillin biosynthesis gene acvA (pcbAB) by amino acids: Implication for involvement of transcription factor PACC," *Appl. Environ. Microbiol.* 64:843–849 (1998).

van de Hombergh et al., "Regulation of acid phosphatases in an *Aspergillus niger* pacC disruption strain," *Mol. Gen. Genet.* 251:542–550 (1996).

Webster et al., "The yeast USAG is a transcriptional enhancer in human HeLa cells in the presence of the GAL4 trans–activator," *Cell* 52:169–178 (1988).

\* cited by examiner

Fig. 1 (page 1 of 4)

| SEQ ID NO | Organism | Sequence (start) |
|---|---|---|
| SEQ ID NO: 1 | A. nidulans | 1 ---------------------------------------------------------------------AMAEEAVAPVAVPTT-- |
| SEQ ID NO: 2 | A. niger | 1 -----------------------------------------------------------------TAPSTTAAPMPTSTS-- |
| SEQ ID NO: 3 | P. chrysogenum | 1 ------------------------------------------------------------MTENHTPSTTQPT--- |
| SEQ ID NO: 4 | Y. lipolytica | 1 ----MASYPYLAQSQPP-QQQQQQQPQQQSQQLPTTAPSAAPQVN--- |
| SEQ ID NO: 5 | C. albicans | 1 MNYNIHPVTYLNADSNTGASEST-ASHHGSKKSPSSDIDVDNAXSPSSFTSSQSPHINAMG |
| SEQ ID NO: 6 | S. cerevisiae | 1 ---MVPLEDLLNKENGTAAPQHSRESIVENGTDVSNVTKKDGLPSPNLSKRSS--- |

| | | |
|---|---|---|
| A. nidulans | 19 | ---QEQPTSQP------------------------------------------------AAA--- |
| A. niger | 24 | ---QDSPSAQ------------------------------------------------QPAQ--- |
| P. chrysogenum | 14 | ---LPAPVAEA------------------------------------------------APIQ--- |
| Y. lipolytica | 43 | NTTANKPLYPASPNSPISPSDYSANMNVGGDSVDMLLSSVSAHHRSSDAGQSDMGSISPST |
| C. albicans | 61 | NSPHSSFTSQSAANSPITDAKQHLVKPTTKPAAFAPSANQSN-TTAPQSYTQPAQQLPTQ |
| S. cerevisiae | 51 | ---DCSKRPRIRCTTEAIGLNGQEDERMSPGS--TSSSCLPYHSTSHLNTPPYD |

| | | |
|---|---|---|
| A. nidulans | 31 | VTTVTSPSVTAT-------------------------------------AAAATAAVAS--- |
| A. niger | 35 | VSSATAASAAAT-------------------------------------AAAA-SAAVAN--- |
| P. chrysogenum | 26 | ANPAPSASVTAT-------------------------------------AAAATAAVNNA--- |
| Y. lipolytica | 104 | AHTTPDATTYKTS-------------------------------DEEDATGKITTPR--- |
| C. albicans | 121 | LHPSLNQAYNNQPSYYLHQPTYGYQQQQQQQQQHQEFNQPSQQYHDHHGYYSNNNILNQNQP |
| S. cerevisiae | 100 | LLGASAVSPTTSSS-------------------------------SDSSSSSPLAQAHN--- |

| | | |
|---|---|---|
| A. nidulans | 53 | -PQANGNAASPVAPASSTSRPAE----ELTCMWQGCSEKLPTPESLYEHVCERHVGRKSTNN |
| A. niger | 57 | -PPMNG-----TTTRPSE----ELSCLWQGCSEKCPSPEALYEHVCERHVGRKSTNN |
| P. chrysogenum | 49 | -PSMNG-----AGE----QLPCQWVGCTEKSPTAESLYEHVCERHVGRKSTNN |
| Y. lipolytica | 133 | SPNTNG-----S-GSDGE-----NLVCKWGPCGKTFGSAEKLYAHLCDAHVGRKCTHN |
| C. albicans | 182 | APQQNPVKPFKKTYKKIRDEDLK--GPFKCLWSNCSIIFETPEILYDHLCDDHVGRKSSNN |
| S. cerevisiae | 128 | -PAGDD-----DDADNDGDSEDI-TLYCKWDNCGMIFNQPELLVNHLCHDHVGRKSHKN |

Fig. 1 (page 1 of 4)

Fig. 1 (page 2 of 4)

Fig. 1 (page 3 of 4)

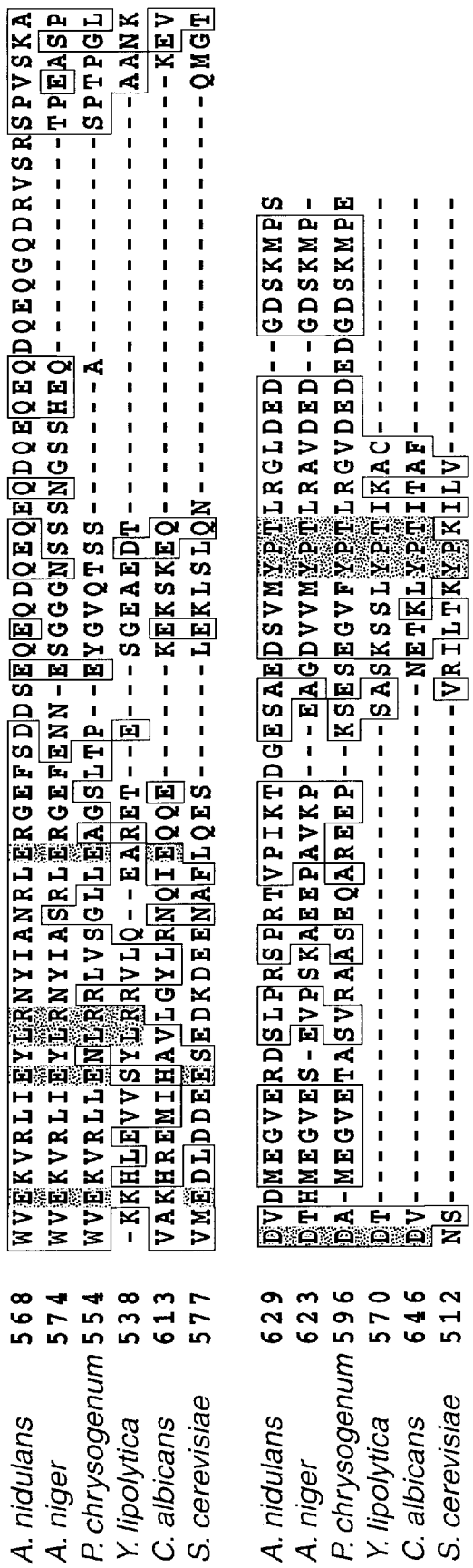
Fig. 1 (page 4 of 4)

```
                          SEQUENCE LISTING

<160> NUMBER OF SEQ ID NOS: 24

<210> SEQ ID NO 1
<211> LENGTH: 678
<212> TYPE: PRT
<213> ORGANISM: Aspergillus nidulans

<400> SEQUENCE: 1

Met Leu Gly Ala Met Ala Glu Glu Ala Val Ala Pro Val Ala Val Pro
 1               5                  10                  15

Thr Thr Gln Glu Gln Pro Thr Ser Gln Pro Ala Ala Ala Gln Val Thr
                20                  25                  30

Thr Val Thr Ser Pro Ser Val Thr Ala Thr Ala Ala Ala Ala Thr Ala
                35                  40                  45

Ala Val Ala Ser Pro Gln Ala Asn Gly Asn Ala Ala Ser Pro Val Ala
            50                  55                  60

Pro Ala Ser Ser Thr Ser Arg Pro Ala Glu Glu Leu Thr Cys Met Trp
65                  70                  75                  80

Gln Gly Cys Ser Glu Lys Leu Pro Thr Pro Glu Ser Leu Tyr Glu His
                85                  90                  95

Val Cys Glu Arg His Val Gly Arg Lys Ser Thr Asn Asn Leu Asn Leu
                100                 105                 110

Thr Cys Gln Trp Gly Ser Cys Arg Thr Thr Thr Val Lys Arg Asp His
                115                 120                 125

Ile Thr Ser His Ile Arg Val His Val Pro Leu Lys Pro His Lys Cys
            130                 135                 140

Asp Phe Cys Gly Lys Ala Phe Lys Arg Pro Gln Asp Leu Lys Lys His
145                 150                 155                 160

Val Lys Thr His Ala Asp Asp Ser Val Leu Val Arg Ser Pro Glu Pro
                165                 170                 175

Gly Ser Arg Asn Pro Asp Met Met Phe Gly Gly Asn Gly Lys Gly Tyr
                180                 185                 190

Ala Ala Ala His Tyr Phe Glu Pro Ala Leu Asn Pro Val Pro Ser Gln
            195                 200                 205

Gly Tyr Ala His Gly Pro Pro Gln Tyr Tyr Gln Ala His His Ala Pro
            210                 215                 220

Gln Pro Ser Asn Pro Ser Tyr Gly Asn Val Tyr Tyr Ala Leu Asn Thr
225                 230                 235                 240

Gly Pro Glu Pro His Gln Ala Ser Tyr Glu Ser Lys Lys Arg Gly Tyr
                245                 250                 255

Asp Ala Leu Asn Glu Phe Phe Gly Asp Leu Lys Arg Arg Gln Phe Asp
                260                 265                 270

Pro Asn Ser Tyr Ala Ala Val Gly Gln Arg Leu Leu Ser Leu Gln Asn
            275                 280                 285

Leu Ser Leu Pro Val Leu Thr Ala Ala Pro Leu Pro Glu Tyr Gln Ala
        290                 295                 300

Met Pro Ala Pro Val Ala Val Ala Ser Gly Pro Tyr Gly Gly Gly Pro
305                 310                 315                 320

His Pro Ala Pro Ala Tyr His Leu Pro Pro Met Ser Asn Val Arg Thr
                325                 330                 335
```

Lys Asn Asp Leu Ile Asn Ile Asp Gln Phe Leu Gln Gln Met Gln Asp
              340                 345                 350

Thr Ile Tyr Glu Asn Asp Asn Val Ala Ala Gly Val Ala Gln
          355                 360                 365

Pro Gly Ala His Tyr Ile His Asn Gly Ile Ser Tyr Arg Thr Thr His
      370                 375                 380

Ser Pro Pro Thr Gln Leu Pro Ser Ala His Ala Thr Thr Gln Thr Thr
385                 390                 395                 400

Ala Gly Pro Ile Ile Ser Asn Thr Ser Ala His Ser Pro Ser Ser
                  405                 410                 415

Thr Pro Ala Leu Thr Pro Pro Ser Ser Ala Gln Ser Tyr Thr Ser Gly
              420                 425                 430

Arg Ser Pro Ile Ser Leu Pro Ser Ala His Arg Val Ser Pro Pro His
              435                 440                 445

Glu Ser Gly Ser Ser Met Tyr Pro Arg Leu Pro Ser Ala Thr Asp Gly
          450                 455                 460

Met Thr Ser Gly Tyr Thr Ala Ala Ser Ala Ala Pro Pro Ser Thr
465                 470                 475                 480

Leu Gly Gly Ile Phe Asp Asn Asp Glu Arg Arg Tyr Thr Gly Gly
                  485                 490                 495

Thr Leu Gln Arg Ala Arg Pro Ala Ser Arg Ala Ala Ser Glu Ser Met
              500                 505                 510

Asp Leu Ser Ser Asp Asp Lys Glu Ser Gly Glu Arg Thr Pro Lys Gln
              515                 520                 525

Ile Ser Ala Ser Leu Ile Asp Pro Ala Leu His Ser Gly Ser Pro Gly
              530                 535                 540

Glu Asp Asp Val Thr Arg Thr Ala Lys Ala Ala Thr Glu Val Ala Glu
545                 550                 555                 560

Arg Ser Asp Val Gln Ser Glu Trp Val Glu Lys Val Arg Leu Ile Glu
                  565                 570                 575

Tyr Leu Arg Asn Tyr Ile Ala Asn Arg Leu Glu Arg Gly Glu Phe Ser
              580                 585                 590

Asp Asp Ser Glu Gln Glu Gln Asp Gln Glu Gln Asp Gln Glu
          595                 600                 605

Gln Glu Gln Asp Gln Glu Gln Gly Gln Asp Arg Val Ser Arg Ser Pro
    610                 615                 620

Val Ser Lys Ala Asp Val Asp Met Glu Gly Val Glu Arg Asp Ser Leu
625                 630                 635                 640

Pro Arg Ser Pro Arg Thr Val Pro Ile Lys Thr Asp Gly Glu Ser Ala
              645                 650                 655

Glu Asp Ser Val Met Tyr Pro Thr Leu Arg Gly Leu Asp Glu Asp Gly
                  660                 665                 670

Asp Ser Lys Met Pro Ser
          675

<210> SEQ ID NO 2
<211> LENGTH: 667
<212> TYPE: PRT
<213> ORGANISM: Aspergillus niger

<400> SEQUENCE: 2

Met Ser Glu Pro Gln Asp Thr Thr Ala Pro Ser Thr Thr Ala Ala
1               5                   10                  15

Pro Met Pro Thr Ser Thr Ser Gln Asp Ser Pro Ser Ala Gln Gln Pro
              20                  25                  30

-continued

```
Ala Gln Val Ser Ser Ala Thr Ala Ala Ser Ala Ala Thr Ala Ala
             35                  40                  45
Ala Ala Ser Ala Ala Val Ala Asn Pro Pro Met Asn Gly Thr Thr Thr
         50                  55                  60
Arg Pro Ser Glu Glu Leu Ser Cys Leu Trp Gln Gly Cys Ser Glu Lys
 65                  70                  75                  80
Cys Pro Ser Pro Glu Ala Leu Tyr Glu His Val Cys Glu Arg His Val
                 85                  90                  95
Gly Arg Lys Ser Thr Asn Asn Leu Asn Leu Thr Cys Gln Trp Gly Ser
             100                 105                 110
Cys Arg Thr Thr Thr Val Lys Arg Asp His Ile Thr Ser His Ile Arg
             115                 120                 125
Val His Val Pro Leu Lys Pro His Lys Cys Asp Phe Cys Gly Lys Ala
             130                 135                 140
Phe Lys Arg Pro Gln Asp Leu Lys Lys His Val Lys Thr His Ala Asp
145                 150                 155                 160
Asp Ser Val Leu Val Arg Ser Pro Glu Pro Gly Ala Arg Asn Pro Asp
                 165                 170                 175
Met Met Phe Gly Gly Ala Lys Gly Tyr Ala Thr Ala Ala His Tyr
             180                 185                 190
Phe Glu Pro Ala Leu Asn Ala Val Pro Ser Gln Gly Tyr Ala His Gly
             195                 200                 205
Ala Pro Gln Tyr Tyr Gln Ser His Pro Pro Gln Pro Ala Asn Pro
             210                 215                 220
Ser Tyr Gly Asn Val Tyr Tyr Ala Leu Asn His Gly Pro Glu Ala Gly
225                 230                 235                 240
His Ala Ser Tyr Glu Ser Lys Lys Arg Gly Tyr Asp Ala Leu Asn Glu
                 245                 250                 255
Phe Phe Gly Asp Leu Lys Arg Arg Gln Phe Asp Pro Asn Ser Tyr Ala
             260                 265                 270
Ala Val Gly Gln Arg Leu Leu Gly Leu Gln Ser Leu Ser Leu Pro Val
             275                 280                 285
Leu Ser Ser Gly Pro Leu Pro Glu Tyr Gln Pro Met Pro Ala Pro Val
    290                 295                 300
Ala Val Gly Gly Gly Tyr Ser Pro Gly Gly Ala Pro Ser Ala Pro
305                 310                 315                 320
Ala Tyr His Leu Pro Pro Met Ser Asn Val Arg Thr Lys Asn Asp Leu
                 325                 330                 335
Ile Asn Ile Asp Gln Phe Leu Gln Gln Met Gln Asp Thr Ile Tyr Glu
             340                 345                 350
Asn Asp Asp Asn Val Ala Ala Gly Val Ala Gln Pro Gly Ala His
             355                 360                 365
Tyr Val His Gly Gly Met Ser Tyr Arg Thr Thr His Ser Pro Pro Thr
    370                 375                 380
Gln Leu Pro Pro Ser His Ala Thr Ala Thr Ser Ser Ala Ser Met Met
385                 390                 395                 400
Pro Asn Pro Ala Thr His Ser Pro Ser Thr Gly Thr Pro Ala Leu Thr
                 405                 410                 415
Pro Pro Ser Ser Ala Gln Ser Tyr Thr Ser Gly Arg Ser Pro Val Ser
             420                 425                 430
Leu Pro Ser Ala Thr Arg Val Ser Pro Pro His His Glu Gly Gly Ser
             435                 440                 445
```

```
Met Tyr Pro Arg Leu Pro Ser Ala Thr Met Ala Asp Ser Met Ala Ala
        450                 455                 460
Gly Tyr Pro Thr Ala Ser Ser Thr Ala Pro Pro Ser Thr Leu Gly Gly
465                 470                 475                 480
Ile Phe Asp His Asp Asp Arg Arg Tyr Thr Gly Gly Thr Leu Gln
                    485                 490                 495
Arg Ala Arg Pro Glu Thr Arg Gln Leu Ser Glu Glu Met Asp Leu Thr
                500                 505                 510
Gln Asp Ser Lys Asp Glu Gly Glu Arg Thr Pro Lys Ala Lys Glu His
            515                 520                 525
Ser Ser Pro Ser Ser Pro Glu Arg Ile Ser Ala Ser Leu Ile Asp Pro
        530                 535                 540
Ala Leu Ser Gly Thr Ala Ala Glu Ala Glu Ala Thr Leu Arg Thr Ala
545                 550                 555                 560
Gln Ala Ala Thr Glu Val Ala Glu Arg Ala Asp Val Gln Trp Val Glu
                565                 570                 575
Lys Val Arg Leu Ile Glu Tyr Leu Arg Asn Tyr Ile Ala Ser Arg Leu
                580                 585                 590
Glu Arg Gly Glu Phe Glu Asn Asn Glu Ser Gly Gly Asn Ser Ser
            595                 600                 605
Ser Asn Gly Ser Ser His Glu Gln Thr Pro Glu Ala Ser Pro Asp Thr
        610                 615                 620
His Met Glu Gly Val Glu Ser Glu Val Pro Ser Lys Ala Glu Glu Pro
625                 630                 635                 640
Ala Val Lys Pro Glu Ala Gly Asp Val Val Met Tyr Pro Thr Leu Arg
                645                 650                 655
Ala Val Asp Glu Asp Gly Asp Ser Lys Met Pro
            660                 665

<210> SEQ ID NO 3
<211> LENGTH: 643
<212> TYPE: PRT
<213> ORGANISM: Penicillium chrysogenum

<400> SEQUENCE: 3

Met Thr Glu Asn His Thr Pro Ser Thr Thr Gln Pro Thr Leu Pro Ala
1               5                   10                  15
Pro Val Ala Glu Ala Ala Pro Ile Gln Ala Asn Pro Ala Pro Ser Ala
                20                  25                  30
Ser Val Thr Ala Thr Ala Ala Ala Thr Ala Ala Val Asn Asn Ala
            35                  40                  45
Pro Ser Met Asn Gly Ala Gly Glu Gln Leu Pro Cys Gln Trp Val Gly
        50                  55                  60
Cys Thr Glu Lys Ser Pro Thr Ala Glu Ser Leu Tyr Glu His Val Cys
65                  70                  75                  80
Glu Arg His Val Gly Arg Lys Ser Thr Asn Asn Leu Asn Leu Thr Cys
                85                  90                  95
Gln Trp Gly Thr Cys Asn Thr Thr Thr Val Lys Arg Asp His Ile Thr
                100                 105                 110
Ser His Ile Arg Val His Val Pro Leu Lys Pro His Lys Cys Asp Phe
            115                 120                 125
Cys Gly Lys Ala Phe Lys Arg Pro Gln Asp Leu Lys Lys His Val Lys
        130                 135                 140
Thr His Ala Asp Asp Ser Glu Ile Arg Ser Pro Glu Pro Gly Met Lys
145                 150                 155                 160
```

-continued

```
His Pro Asp Met Met Phe Pro Gln Asn Pro Arg Gly Ser Pro Ala Ala
            165                 170                 175

Thr His Tyr Phe Glu Ser Pro Ile Asn Gly Ile Asn Gly Gln Tyr Ser
            180                 185                 190

His Ala Pro Pro Pro Gln Tyr Tyr Gln Pro His Pro Pro Gln Ala
            195                 200                 205

Pro Asn Pro His Ser Tyr Gly Asn Leu Tyr Tyr Ala Leu Ser Gln Gly
    210                 215                 220

Gln Glu Gly Gly His Pro Tyr Asp Arg Lys Arg Gly Tyr Asp Ala Leu
225                 230                 235                 240

Asn Glu Phe Phe Gly Asp Leu Lys Arg Arg Gln Phe Asp Pro Asn Ser
                245                 250                 255

Tyr Ala Ala Val Gly Gln Arg Leu Leu Gly Leu Gln Ala Leu Gln Leu
                260                 265                 270

Pro Phe Leu Ser Gly Pro Ala Pro Glu Tyr Gln Gln Met Pro Ala Pro
            275                 280                 285

Val Ala Val Gly Gly Gly Gly Gly Tyr Gly Gly Ala Pro Gln
    290                 295                 300

Pro Pro Gly Tyr His Leu Pro Pro Met Ser Asn Val Arg Thr Lys Asn
305                 310                 315                 320

Asp Leu Ile Asn Ile Asp Gln Phe Leu Glu Gln Met Gln Asn Thr Ile
                325                 330                 335

Tyr Glu Ser Asp Glu Asn Val Ala Ala Ala Gly Val Ala Gln Pro Gly
            340                 345                 350

Ala His Tyr Val His Gly Gly Met Asn His Arg Thr Thr His Ser Pro
            355                 360                 365

Pro Thr His Ser Arg Gln Ala Thr Leu Leu Gln Leu Pro Ser Ala Pro
    370                 375                 380

Met Ala Ala Thr Ala His Ser Pro Ser Val Gly Thr Pro Ala Leu
385                 390                 395                 400

Thr Pro Pro Ser Ser Ala Gln Ser Tyr Thr Ser Asn Arg Ser Pro Ile
            405                 410                 415

Ser Leu His Ser Ser Arg Val Ser Pro Pro His Glu Glu Ala Ala Pro
            420                 425                 430

Gly Met Tyr Pro Arg Leu Pro Ala Ala Ile Cys Ala Asp Ser Met Thr
        435                 440                 445

Ala Gly Tyr Pro Thr Ala Ser Gly Ala Ala Pro Pro Ser Thr Leu Ser
        450                 455                 460

Gly Ala Tyr Asp His Asp Asp Arg Arg Tyr Thr Gly Gly Thr Leu
465                 470                 475                 480

Gln Arg Ala Arg Pro Ala Glu Arg Ala Ala Thr Glu Asp Arg Met Asp
            485                 490                 495

Ile Ser Gln Asp Ser Lys His Asp Gly Glu Arg Thr Pro Lys Ala Met
            500                 505                 510

His Ile Ser Ala Ser Leu Ile Asp Pro Ala Leu Ser Gly Thr Ser Ser
        515                 520                 525

Asp Pro Glu Gln Glu Ser Ala Lys Arg Thr Ala Ala Thr Ala Thr Glu
            530                 535                 540

Val Ala Glu Arg Asp Val Asn Val Ala Trp Val Glu Lys Val Arg Leu
545                 550                 555                 560

Leu Glu Asn Leu Arg Arg Leu Val Ser Gly Leu Leu Glu Ala Gly Ser
                565                 570                 575
```

```
Leu Thr Pro Glu Tyr Gly Val Gln Thr Ser Ser Ala Ser Pro Thr Pro
            580                 585                 590

Gly Leu Asp Ala Met Glu Gly Val Glu Thr Ala Ser Val Arg Ala Ala
            595                 600                 605

Ser Glu Gln Ala Arg Glu Pro Lys Ser Glu Ser Glu Gly Val Phe
            610                 615                 620

Tyr Pro Thr Leu Arg Gly Val Asp Glu Asp Asp Gly Asp Ser Lys
625                 630                 635                 640

Met Pro Glu

<210> SEQ ID NO 4
<211> LENGTH: 585
<212> TYPE: PRT
<213> ORGANISM: Yarrowia lipolytica

<400> SEQUENCE: 4

Met Ala Ser Tyr Pro Tyr Leu Ala Gln Ser Gln Pro Gln Gln Gln
  1               5                  10                  15

Gln Gln Gln Gln Gln Gln Pro Gln Gln Gln Ser Gln Gln Leu Pro Thr
                20                  25                  30

Thr Ala Pro Ser Ala Ala Pro Gln Val Asn Asn Thr Thr Ala Asn Lys
                35                  40                  45

Pro Leu Tyr Pro Ala Ser Pro Asn Ser Pro Ile Ser Pro Ser Asp Tyr
 50                  55                  60

Ser Ala Asn Met Asn Val Gly Gly Asp Ser Val Asp Met Leu Leu Ser
 65                  70                  75                  80

Ser Val Ser Ala His His Arg Ser Ser Asp Ala Gly Gln Ser Asp Met
                85                  90                  95

Gly Ser Ile Ser Pro Ser Thr Ala His Thr Thr Pro Asp Ala Thr Thr
                100                 105                 110

Tyr Lys Thr Ser Asp Glu Glu Asp Ala Thr Gly Lys Ile Thr Thr Pro
                115                 120                 125

Arg Ser Glu Gly Ser Pro Asn Thr Asn Gly Ser Gly Ser Asp Gly Glu
                130                 135                 140

Asn Leu Val Cys Lys Trp Gly Pro Cys Gly Lys Thr Phe Gly Ser Ala
145                 150                 155                 160

Glu Lys Leu Tyr Ala His Leu Cys Asp Ala His Val Gly Arg Lys Cys
                165                 170                 175

Thr His Asn Leu Ser Leu Val Cys Asn Trp Asp Asn Cys Gly Ile Val
                180                 185                 190

Thr Val Lys Arg Asp His Ile Thr Ser His Ile Arg Val His Val Pro
                195                 200                 205

Leu Lys Pro Tyr Lys Cys Asp Phe Cys Thr Lys Ser Phe Lys Arg Pro
                210                 215                 220

Gln Asp Leu Lys Lys His Val Lys Thr His Ala Asp Asp Asn Glu Gln
225                 230                 235                 240

Ala His Asn Ala Tyr Ala Lys Pro His Met Gln His Thr His Gln Gln
                245                 250                 255

Gln Gln Gln Gln Gln Arg Tyr Met Gln Tyr Pro Thr Tyr Ala Ser Gly
                260                 265                 270

Tyr Glu Tyr Pro Tyr Tyr Arg Tyr Ser Gln Pro Gln Val Gln Val Pro
                275                 280                 285

Met Val Pro Ser Tyr Ala Ala Val Gly His Met Pro Thr Pro Pro Met
                290                 295                 300
```

```
His Pro His Ala Pro Ile Asp Arg Lys Arg Gln Trp Asp Thr Thr Ser
305                 310                 315                 320

Asp Phe Phe Asp Asp Ile Lys Arg Ala Arg Val Thr Pro Asn Tyr Ser
            325                 330                 335

Ser Asp Ile Ala Ser Arg Leu Ser Thr Ile Glu Gln Tyr Ile Gly Ile
            340                 345                 350

Gln Gly Gln Gln Gln Ala Ser Pro Thr Pro Gln Thr Ala Thr Thr
        355                 360                 365

Thr Ser Ala Thr Pro Ala Pro Ala Ala Pro His Gln Ala Thr Pro Pro
370                 375                 380

Gln Gln Gln Leu Pro Ser Phe Lys Gln Gly Asp Tyr Gln Glu Thr Asp
385                 390                 395                 400

Gln Phe Leu Asn Gln Leu Gly Ser Asn Ile Tyr Gly Asn Ile Lys Ser
            405                 410                 415

Val Asp Pro Gln Tyr Glu Ala Pro Ala Glu Phe His Leu Pro His Pro
            420                 425                 430

Met Gly Tyr Arg Tyr Ala Phe Ser His Ala Pro Ala Pro His Gly Ala
            435                 440                 445

Ala Pro Val Ala Pro Gln Val Ala Pro Pro Ala His Pro Gly Val His
        450                 455                 460

Gly Val Ser Ala Pro His Tyr Pro Asp Leu Ser Tyr Ser Arg Ser Thr
465                 470                 475                 480

Val Pro Gln Leu Ser Ser Arg Phe Glu Asp Val Arg Gln Met Ser Val
            485                 490                 495

Gly Val Thr Gln Arg Ala Ala Arg Thr Thr Asn Val Glu Glu Ser Asp
            500                 505                 510

Asp Asp Asp Glu Leu Val Glu Gly Phe Gly Lys Met Ala Ile Ala Asp
        515                 520                 525

Ser Lys Ala Met Gln Val Ala Gln Met Lys Lys His Leu Glu Val Val
        530                 535                 540

Ser Tyr Leu Arg Arg Val Leu Gln Glu Ala Arg Glu Thr Glu Ser Gly
545                 550                 555                 560

Glu Ala Glu Asp Thr Ala Ala Asn Lys Asp Thr Ser Ala Ser Lys Ser
            565                 570                 575

Ser Leu Tyr Pro Thr Ile Lys Ala Cys
            580                 585

<210> SEQ ID NO 5
<211> LENGTH: 659
<212> TYPE: PRT
<213> ORGANISM: Candida albicans

<400> SEQUENCE: 5

Met Asn Tyr Asn Ile His Pro Val Thr Tyr Leu Asn Ala Asp Ser Asn
1               5                   10                  15

Thr Gly Ala Ser Glu Ser Thr Ala Ser His His Gly Ser Lys Lys Ser
            20                  25                  30

Pro Ser Ser Asp Ile Asp Val Asp Asn Ala Xaa Ser Pro Ser Ser Phe
        35                  40                  45

Thr Ser Ser Gln Ser Pro His Ile Asn Ala Met Gly Asn Ser Pro His
    50                  55                  60

Ser Ser Phe Thr Ser Gln Ser Ala Ala Asn Ser Pro Ile Thr Asp Ala
65                  70                  75                  80

Lys Gln His Leu Val Lys Pro Thr Thr Lys Pro Ala Ala Phe Ala
            85                  90                  95
```

-continued

```
Pro Ser Ala Asn Gln Ser Asn Thr Thr Ala Pro Gln Ser Tyr Thr Gln
            100                 105                 110
Pro Ala Gln Gln Leu Pro Thr Gln Leu His Pro Ser Leu Asn Gln Ala
            115                 120                 125
Tyr Asn Asn Gln Pro Ser Tyr Tyr Leu His Gln Pro Thr Tyr Gly Tyr
            130                 135                 140
Gln Gln Gln Gln Gln Gln Gln His Gln Glu Phe Asn Gln Pro Ser
145                 150                 155                 160
Gln Gln Tyr His Asp His His Gly Tyr Tyr Ser Asn Asn Asn Ile Leu
                165                 170                 175
Asn Gln Asn Gln Pro Ala Pro Gln Gln Asn Pro Val Lys Pro Phe Lys
            180                 185                 190
Lys Thr Tyr Lys Lys Ile Arg Asp Glu Asp Leu Lys Gly Pro Phe Lys
            195                 200                 205
Cys Leu Trp Ser Asn Cys Ser Ile Ile Phe Glu Thr Pro Glu Ile Leu
            210                 215                 220
Tyr Asp His Leu Cys Asp Asp His Val Gly Arg Lys Ser Ser Asn Asn
225                 230                 235                 240
Leu Ser Leu Thr Cys Leu Trp Glu Asn Cys Gly Thr Thr Val Lys
            245                 250                 255
Arg Asp His Ile Thr Ser His Leu Arg Val His Val Pro Leu Lys Pro
            260                 265                 270
Phe His Cys Asp Leu Cys Pro Lys Ser Phe Lys Arg Pro Gln Asp Leu
            275                 280                 285
Lys Lys His Ser Lys Thr His Ala Glu Asp His Pro Lys Lys Leu Lys
            290                 295                 300
Lys Ala Gln Arg Glu Leu Met Lys Gln Gln Lys Glu Ala Lys Gln
305                 310                 315                 320
Gln Gln Lys Leu Ala Asn Lys Arg Ala Asn Ser Met Asn Ala Thr Thr
            325                 330                 335
Ala Ser Asp Leu Gln Leu Asn Tyr Tyr Ser Gly Asn Pro Ala Asp Gly
            340                 345                 350
Leu Asn Tyr Asp Asp Thr Ser Lys Lys Arg Arg Tyr Glu Asn Asn Ser
            355                 360                 365
Gln His Asn Met Tyr Val Val Asn Ser Ile Leu Asn Asp Phe Asn Phe
            370                 375                 380
Gln Gln Met Ala Gln Ala Pro Gln Gln Pro Gly Val Val Gly Thr Ala
385                 390                 395                 400
Gly Ser Ala Glu Phe Thr Thr Lys Arg Met Lys Ala Gly Thr Glu Tyr
            405                 410                 415
Asn Ile Asp Val Phe Asn Lys Leu Asn His Leu Asp Asp His Leu His
            420                 425                 430
His His His Pro Gln Gln Gln His Pro Gln Gln Tyr Gly Gly Asn
            435                 440                 445
Ile Tyr Glu Ala Glu Lys Phe Phe Asn Ser Leu Ser Asn Ser Ile Asp
            450                 455                 460
Met Gln Tyr Gln Asn Met Ser Thr Gln Tyr Gln Gln His Ala Gly
465                 470                 475                 480
Ser Thr Phe Ala Gln Gln Lys Pro Thr Gln Gln Ala Ser Gly Gln Leu
            485                 490                 495
Tyr Pro Ser Leu Pro Thr Ile Gly Asn Gly Ser Tyr Thr Ser Gly Ser
            500                 505                 510
```

Ser His Lys Glu Gly Leu Val Asn Asn His Asn Gly Tyr Leu Pro Ser
            515                 520                 525

Tyr Pro Gln Ile Asn Arg Ser Leu Pro Tyr Ser Ser Gly Val Ala Gln
        530                 535                 540

Gln Pro Pro Ser Ala Leu Glu Phe Gly Gly Val Ser Thr Tyr Gln Lys
545                 550                 555                 560

Ser Ala Gln Ser Tyr Glu Glu Asp Ser Ser Asp Ser Ser Glu Glu Asp
            565                 570                 575

Asp Tyr Ser Thr Ser Ser Glu Asp Glu Leu Asp Thr Leu Phe Asp Lys
            580                 585                 590

Leu Asn Ile Asp Asp Asn Lys Val Glu Glu Val Thr Ile Asp Gly Phe
            595                 600                 605

Asn Leu Lys Asp Val Ala Lys His Arg Glu Met Ile His Ala Val Leu
            610                 615                 620

Gly Tyr Leu Arg Asn Gln Ile Glu Gln Gln Glu Lys Glu Lys Ser Lys
625                 630                 635                 640

Glu Gln Lys Glu Val Asp Val Asn Glu Thr Lys Leu Tyr Pro Thr Ile
                645                 650                 655

Thr Ala Phe

<210> SEQ ID NO 6
<211> LENGTH: 625
<212> TYPE: PRT
<213> ORGANISM: Saccharomyces cerevisiae

<400> SEQUENCE: 6

Met Val Pro Leu Glu Asp Leu Leu Asn Lys Glu Asn Gly Thr Ala Ala
1               5                   10                  15

Pro Gln His Ser Arg Glu Ser Ile Val Glu Asn Gly Thr Asp Val Ser
            20                  25                  30

Asn Val Thr Lys Lys Asp Gly Leu Pro Ser Pro Asn Leu Ser Lys Arg
        35                  40                  45

Ser Ser Asp Cys Ser Lys Arg Pro Arg Ile Arg Cys Thr Thr Glu Ala
    50                  55                  60

Ile Gly Leu Asn Gly Gln Glu Asp Glu Arg Met Ser Pro Gly Ser Thr
65                  70                  75                  80

Ser Ser Ser Cys Leu Pro Tyr His Ser Thr Ser His Leu Asn Thr Pro
                85                  90                  95

Pro Tyr Asp Leu Leu Gly Ala Ser Ala Val Ser Pro Thr Thr Ser Ser
            100                 105                 110

Ser Ser Asp Ser Ser Ser Ser Pro Leu Ala Gln Ala His Asn Pro
            115                 120                 125

Ala Gly Asp Asp Asp Ala Asp Asn Asp Gly Asp Ser Glu Asp Ile
    130                 135                 140

Thr Leu Tyr Cys Lys Trp Asp Asn Cys Gly Met Ile Phe Asn Gln Pro
145                 150                 155                 160

Glu Leu Leu Tyr Asn His Leu Cys His Asp His Val Gly Arg Lys Ser
                165                 170                 175

His Lys Asn Leu Gln Leu Asn Cys His Trp Gly Asp Cys Thr Thr Lys
            180                 185                 190

Thr Glu Lys Arg Asp His Ile Thr Ser His Leu Arg Val His Val Pro
        195                 200                 205

Leu Lys Pro Phe Gly Cys Ser Thr Cys Ser Lys Lys Phe Lys Arg Pro
    210                 215                 220

-continued

```
Gln Asp Leu Lys Lys His Leu Lys Ile His Leu Glu Ser Gly Gly Ile
225                 230                 235                 240

Leu Lys Arg Lys Arg Gly Pro Lys Trp Gly Ser Lys Arg Thr Ser Lys
            245                 250                 255

Lys Asn Lys Ser Cys Ala Ser Asp Ala Val Ser Ser Cys Ser Ala Ser
            260                 265                 270

Val Pro Ser Ala Ile Ala Gly Ser Phe Lys Ser His Ser Thr Ser Pro
        275                 280                 285

Gln Ile Leu Pro Pro Leu Pro Val Gly Ile Ser Gln His Leu Pro Ser
        290                 295                 300

Gln Gln Gln Gln Arg Ala Ile Ser Leu Asn Gln Leu Cys Ser Asp Glu
305                 310                 315                 320

Leu Ser Gln Tyr Lys Pro Val Tyr Ser Pro Gln Leu Ser Ala Arg Leu
            325                 330                 335

Gln Thr Ile Leu Pro Pro Leu Tyr Tyr Asn Asn Gly Ser Thr Val Ser
            340                 345                 350

Gln Gly Ala Asn Ser Arg Ser Met Asn Val Tyr Glu Asp Gly Cys Ser
        355                 360                 365

Asn Lys Thr Ile Ala Asn Ala Thr Gln Phe Phe Thr Lys Leu Ser Arg
370                 375                 380

Asn Met Thr Asn Asn Tyr Ile Leu Gln Gln Ser Gly Gly Ser Thr Glu
385                 390                 395                 400

Ser Ser Ser Ser Ser Gly Arg Ile Pro Val Ala Gln Thr Ser Tyr Val
            405                 410                 415

Gln Pro Pro Asn Ala Pro Ser Tyr Gln Ser Val Gln Gly Gly Ser Ser
            420                 425                 430

Ile Ser Ala Thr Ala Asn Thr Ala Thr Tyr Val Pro Val Arg Leu Ala
        435                 440                 445

Lys Tyr Pro Thr Gly Pro Ser Leu Thr Glu His Leu Pro Pro Leu His
        450                 455                 460

Ser Asn Thr Ala Gly Gly Val Phe Asn Arg Gln Ser Gln Tyr Ala Met
465                 470                 475                 480

Pro His Tyr Pro Ser Val Arg Ala Ala Pro Ser Tyr Ser Ser Ser Gly
            485                 490                 495

Cys Ser Ile Leu Pro Pro Leu Gln Ser Lys Ile Pro Met Leu Pro Ser
            500                 505                 510

Arg Arg Thr Met Ala Gly Gly Thr Ser Leu Lys Pro Asn Trp Glu Phe
        515                 520                 525

Ser Leu Asn Gln Lys Ser Cys Thr Asn Asp Ile Ile Met Ser Lys Leu
530                 535                 540

Ala Ile Glu Glu Val Asp Asp Glu Ser Glu Ile Glu Asp Asp Phe Val
545                 550                 555                 560

Glu Met Leu Gly Ile Val Asn Ile Ile Lys Asp Tyr Leu Leu Cys Cys
            565                 570                 575

Val Met Glu Asp Leu Asp Asp Glu Glu Ser Glu Asp Lys Asp Glu Glu
            580                 585                 590

Asn Ala Phe Leu Gln Glu Ser Leu Glu Lys Leu Ser Leu Gln Asn Gln
        595                 600                 605

Met Gly Thr Asn Ser Val Arg Ile Leu Thr Lys Tyr Pro Lys Ile Leu
        610                 615                 620

Val
625
```

-continued

```
<210> SEQ ID NO 7
<211> LENGTH: 815
<212> TYPE: PRT
<213> ORGANISM: Artificial Sequence
<220> FEATURE:
<223> OTHER INFORMATION: Synthetic primer based on Aspergillus nidulans
      and herpes virus

<400> SEQUENCE: 7

Met Ser Ser Arg Gly Ala Met Ala Glu Glu Ala Val Ala Pro Val Ala
1               5                   10                  15

Val Pro Thr Thr Gln Glu Gln Pro Thr Ser Gln Pro Ala Ala Ala Gln
            20                  25                  30

Val Thr Thr Val Thr Ser Pro Ser Val Thr Ala Thr Ala Ala Ala Ala
        35                  40                  45

Thr Ala Ala Val Ala Ser Pro Gln Ala Asn Gly Asn Ala Ala Ser Pro
    50                  55                  60

Val Ala Pro Ala Ser Ser Thr Ser Arg Pro Ala Glu Glu Leu Thr Cys
65                  70                  75                  80

Met Trp Gln Gly Cys Ser Glu Lys Leu Pro Thr Pro Glu Ser Leu Tyr
                85                  90                  95

Glu His Val Cys Glu Arg His Val Gly Arg Lys Ser Thr Asn Asn Leu
            100                 105                 110

Asn Leu Thr Cys Gln Trp Gly Ser Cys Arg Thr Thr Thr Val Lys Arg
        115                 120                 125

Asp His Ile Thr Ser His Ile Arg Val His Val Pro Leu Lys Pro His
    130                 135                 140

Lys Cys Asp Phe Cys Gly Lys Ala Phe Lys Arg Pro Gln Asp Leu Lys
145                 150                 155                 160

Lys His Val Lys Thr His Ala Asp Asp Ser Val Leu Val Arg Ser Pro
                165                 170                 175

Glu Pro Gly Ser Arg Asn Pro Asp Met Met Phe Gly Gly Asn Gly Lys
            180                 185                 190

Gly Tyr Ala Ala Ala His Tyr Phe Glu Pro Ala Leu Asn Pro Val Pro
        195                 200                 205

Ser Gln Gly Tyr Ala His Gly Pro Pro Gln Tyr Tyr Gln Ala His His
    210                 215                 220

Ala Pro Gln Pro Ser Asn Pro Ser Tyr Gly Asn Val Tyr Tyr Ala Leu
225                 230                 235                 240

Asn Thr Gly Pro Glu Pro His Gln Ala Ser Tyr Glu Ser Lys Lys Arg
                245                 250                 255

Gly Tyr Asp Ala Leu Asn Glu Phe Phe Gly Asp Leu Lys Arg Arg Gln
            260                 265                 270

Phe Asp Pro Asn Ser Tyr Ala Ala Val Gly Gln Arg Leu Leu Ser Leu
        275                 280                 285

Gln Asn Leu Ser Leu Pro Val Leu Thr Ala Ala Pro Leu Pro Glu Tyr
    290                 295                 300

Gln Ala Met Pro Ala Pro Val Ala Val Ala Ser Gly Pro Tyr Gly Gly
305                 310                 315                 320

Gly Pro His Pro Ala Pro Ala Tyr His Leu Pro Pro Met Ser Asn Val
                325                 330                 335

Arg Thr Lys Asn Asp Leu Ile Asn Ile Asp Gln Phe Leu Gln Gln Met
            340                 345                 350

Gln Asp Thr Ile Tyr Glu Asn Asp Asp Asn Val Ala Ala Ala Gly Val
        355                 360                 365
```

-continued

```
Ala Gln Pro Gly Ala His Tyr Ile His Asn Gly Ile Ser Tyr Arg Thr
    370                 375                 380

Thr His Ser Pro Pro Thr Gln Leu Pro Ser Ala His Ala Thr Thr Gln
385                 390                 395                 400

Thr Thr Ala Gly Pro Ile Ile Ser Asn Thr Ser Ala His Ser Pro Ser
                405                 410                 415

Ser Ser Thr Pro Ala Leu Thr Pro Pro Ser Ser Ala Gln Ser Tyr Thr
                420                 425                 430

Ser Gly Arg Ser Pro Ile Ser Leu Pro Ser Ala His Arg Val Ser Pro
            435                 440                 445

Pro His Glu Ser Gly Ser Ser Met Tyr Pro Arg Leu Pro Ser Ala Thr
            450                 455                 460

Asp Gly Met Thr Ser Gly Tyr Gly Ser Pro Pro Pro Pro Pro Pro Pro
465                 470                 475                 480

Pro Pro Pro Pro Ile Lys Val Ala Pro Pro Thr Asp Val Ser Leu Gly
                485                 490                 495

Asp Glu Leu His Leu Asp Gly Glu Asp Val Ala Met Ala His Ala Asp
                500                 505                 510

Ala Leu Asp Asp Phe Asp Leu Asp Met Leu Gly Asp Gly Asp Ser Pro
            515                 520                 525

Gly Pro Gly Phe Thr Pro His Asp Ser Ala Pro Tyr Gly Ala Leu Asp
            530                 535                 540

Met Ala Asp Phe Glu Phe Glu Gln Met Phe Thr Asp Ala Leu Gly Ile
545                 550                 555                 560

Asp Glu Tyr Gly Gly Asp Ile Lys Val Ala Pro Pro Thr Asp Val Ser
                565                 570                 575

Leu Gly Asp Glu Leu His Leu Asp Gly Glu Asp Val Ala Met Ala His
                580                 585                 590

Ala Asp Ala Leu Asp Asp Phe Asp Leu Asp Met Leu Gly Asp Gly Asp
            595                 600                 605

Ser Pro Gly Pro Gly Phe Thr Pro His Asp Ser Ala Pro Tyr Gly Ala
            610                 615                 620

Leu Asp Met Ala Asp Phe Glu Phe Glu Gln Met Phe Thr Asp Ala Leu
625                 630                 635                 640

Gly Ile Asp Glu Tyr Gly Gly Asp Ile Lys Val Ala Pro Pro Thr Asp
                645                 650                 655

Val Ser Leu Gly Asp Glu Leu His Leu Asp Gly Glu Asp Val Ala Met
                660                 665                 670

Ala His Ala Asp Ala Leu Asp Asp Phe Asp Leu Asp Met Leu Gly Asp
            675                 680                 685

Gly Asp Ser Pro Gly Pro Gly Phe Thr Pro His Asp Ser Ala Pro Tyr
            690                 695                 700

Gly Ala Leu Asp Met Ala Asp Phe Glu Phe Glu Gln Met Phe Thr Asp
705                 710                 715                 720

Ala Leu Gly Ile Asp Glu Tyr Gly Gly Asp Ile Lys Val Ala Pro Pro
                725                 730                 735

Thr Asp Val Ser Leu Gly Asp Glu Leu His Leu Asp Gly Glu Asp Val
                740                 745                 750

Ala Met Ala His Ala Asp Ala Leu Asp Asp Phe Asp Leu Asp Met Leu
            755                 760                 765

Gly Asp Gly Asp Ser Pro Gly Pro Gly Phe Thr Pro His Asp Ser Ala
            770                 775                 780
```

```
Pro Tyr Gly Ala Leu Asp Met Ala Asp Phe Glu Phe Glu Gln Met Phe
785                 790                 795                 800

Thr Asp Ala Leu Gly Ile Asp Glu Tyr Gly Gly Asp Gly Leu Gln
                805                 810                 815

<210> SEQ ID NO 8
<211> LENGTH: 32
<212> TYPE: DNA
<213> ORGANISM: Artificial Sequence
<220> FEATURE:
<223> OTHER INFORMATION: Synthetic primer based on Aspergillus nidulans

<400> SEQUENCE: 8
aactgcagta gttgaccgtg tgattgggtt ct                                    32

<210> SEQ ID NO 9
<211> LENGTH: 30
<212> TYPE: DNA
<213> ORGANISM: Artificial Sequence
<220> FEATURE:
<223> OTHER INFORMATION: Synthetic primer based on Aspergillus nidulans

<400> SEQUENCE: 9
ccggaattct ttgtaaactg gcttgaagat                                       30

<210> SEQ ID NO 10
<211> LENGTH: 35
<212> TYPE: DNA
<213> ORGANISM: Artificial Sequence
<220> FEATURE:
<223> OTHER INFORMATION: Synthetic oligonucleotide encoding proline rich
      motif

<400> SEQUENCE: 10 gatcccccccc ccctcctcca cccccacccc ctccc                                35

<210> SEQ ID NO 11
<211> LENGTH: 31
<212> TYPE: DNA
<213> ORGANISM: Artificial Sequence
<220> FEATURE:
<223> OTHER INFORMATION: Synthetic oligonucleotide encoding proline rich
      motif

<400> SEQUENCE: 11 gggaggggt ggggtggag gagggggggg g                                       31

<210> SEQ ID NO 12
<211> LENGTH: 30
<212> TYPE: DNA
<213> ORGANISM: Artificial Sequence
<220> FEATURE:
<223> OTHER INFORMATION: Synthetic primer based on herpes simplex virus

<400> SEQUENCE: 12
cgcgatatca aagtcgcccc cccgaccgat                                       30

<210> SEQ ID NO 13
<211> LENGTH: 30
<212> TYPE: DNA
<213> ORGANISM: Synthetic primer based on Aspergillus nidulans

<400> SEQUENCE: 13
cgcgatatcc ccaccgtact cgtcaattcc                                       30
```

<210> SEQ ID NO 14
<211> LENGTH: 30
<212> TYPE: DNA
<213> ORGANISM: Artificial Sequence
<220> FEATURE:
<223> OTHER INFORMATION: Synthetic primer based on Aspergillus nidulans

<400> SEQUENCE: 14
tgctctagag gcgccatggc cgaagaagcg         30

<210> SEQ ID NO 15
<211> LENGTH: 30
<212> TYPE: DNA
<213> ORGANISM: Aspergillus nidulans

<400> SEQUENCE: 15
cgcggatccg taaccagaag tcataccgtc         30

<210> SEQ ID NO 16
<211> LENGTH: 1413
<212> TYPE: DNA
<213> ORGANISM: Artificial Sequence
<220> FEATURE:
<223> OTHER INFORMATION: Synthetic primer based on Aspergillus nidulans

<400> SEQUENCE: 16

| | | | | | |
|---|---|---|---|---|---|
| tctagaggcg | ccatggccga | agaagcggtc | gctcctgtag | ctgtgcctac | gacccaagaa | 60 |
| caaccaacct | ctcaacccgc | cgctgcgcag | gttacaactg | tcacttcgcc | ctctgtgact | 120 |
| gcaacagcgg | cggctgcgac | agctgctgtg | gccagtcccc | aagctaatgg | caatgctgcc | 180 |
| tctcctgtcg | ccctgcgtc | gtcaacatct | cgtccagcgg | aagaactcac | ttgcatgtgg | 240 |
| caaggctgct | ctgagaagct | ccctactcca | gaatccttat | acgaacatgt | ctgcgagcgt | 300 |
| cacgttggcc | gaaagagcac | gaacaacctc | aacctgactt | gtcaatgggg | tagctgtcgt | 360 |
| actactactg | tgaaacgcga | ccatatcacc | tctcatatcc | gggtgcacgt | tcctctcaag | 420 |
| ccgcacaagt | gtgatttctg | tggaaaagcg | ttcaagcgtc | cccaggattt | gaagaagcat | 480 |
| gttaagacgc | acgctgatga | ctcggtcctg | gtacggtcgc | cagagcctgg | atctcgcaac | 540 |
| ccagatatga | tgttcggagg | aaatggcaag | ggctatgctg | ctgcgcacta | ttttgagcct | 600 |
| gctctcaacc | ctgttcccag | ccaaggctac | gctcatggtc | ctccccagta | ttaccaggcc | 660 |
| catcacgctc | cccagccatc | gaacccgtct | tacggcaacg | tctactacgc | tctgaatacc | 720 |
| ggcccagagc | ctcaccaagc | gtcgtatgaa | tccaagaagc | ggggttatga | tgcgcttaat | 780 |
| gagttctttg | gtgacctcaa | gcgccgacaa | tttgaccecta | attcctacgc | tgccgtgggc | 840 |
| cagcgcctgc | tcagtttgca | gaacttgtcc | ctgcctgttt | taacggctgc | gcctctgccc | 900 |
| gagtaccagg | caatgcctgc | tcctgtggct | gttgctagtg | gtccatatgg | tggcggccct | 960 |
| caccctgcgc | cggcatatca | tcttccacca | atgagcaacg | tccgaaccaa | gaacgacttg | 1020 |
| atcaacatcg | accagttcct | gcagcaaatg | caggacacaa | tatatgagaa | cgatgataat | 1080 |
| gtcgctgcgc | ctggtgtcgc | tcaacctgga | gcccattaca | ttcataacgg | cataagctac | 1140 |
| cgcactacac | actcgcctcc | gacacaactt | ccctcggcac | atgccacaac | ccagacgact | 1200 |
| gctggtccta | ttatctcaaa | cacatctgcg | cactccccctt | cgtctagcac | tccggctttg | 1260 |
| acaccgccct | caagtgcgca | gtcgtacact | tcaggtcgct | ctcccatttc | acttccgtct | 1320 |
| gctcatcgcg | tttctccgcc | tcatgaaagc | ggctccagca | tgtaccctcg | tctcccttcg | 1380 |
| gcgactgacg | gtatgacttc | tggttacgga | tcc | | | 1413 |

<210> SEQ ID NO 17
<211> LENGTH: 37
<212> TYPE: DNA
<213> ORGANISM: Artificial Sequence
<220> FEATURE:
<223> OTHER INFORMATION: Synthetic primer based on Aspergillus nidulans

<400> SEQUENCE: 17
ataagaatgc ggccgccctc tgcattattg tcttatc                           37

<210> SEQ ID NO 18
<211> LENGTH: 30
<212> TYPE: DNA
<213> ORGANISM: Artificial Sequence
<220> FEATURE:
<223> OTHER INFORMATION: Synthetic primer based on Aspergillus nidulans

<400> SEQUENCE: 18
tgctctagaa gacattgttg ctatagctgt                                   30

<210> SEQ ID NO 19
<211> LENGTH: 678
<212> TYPE: DNA
<213> ORGANISM: Aspergillus nidulans

<400> SEQUENCE: 19
gcggccgccc tctgcattat tgtcttatcc gctattcctg gtgttttgt tgtcttacta    60 cttttttgtgt cgttgaaatt cttactaggc gttgtgaatc tggatcggat catgctattt   120
tgaggtgtaa tgcatgggtc aaattttctc gagtttcaaa cgaggcagaa gagagatgca   180
gataaatctt gagttttatc atgcagcgaa cgttaccact tatagtttcc ggcagagcac   240
gtaggtcggc ccggcgtcat gtgtagcggg ggagctccag gaccttgagg acgaaaatgg   300
gacggcgatg tataactcca tggaggaacg gagcgtgatt ttgtactgtc tgatccgagg   360
ctaatgagaa agcggaggtt caatgttccc ccggttgatg tcctgaagca gcgaggcccg   420
aagtatcccg tcgtggacat gacatcagtg gtccgactcc cgccgaaccc tcctccttca   480
ccggcagccc caccatgtcg ccaaagcaaa tggtagctct gcgattctgg ataccccgcc   540
actcaccgtg atacaatttc agcatttgcg aggtggtctg gtctcctgac gcgctttatt   600
tatccctggt ctctccccac tagctgttcc tgcccgtcca tctctctccg tacagctata   660
gcaacaatgt cttctaga                                                678

<210> SEQ ID NO 20
<211> LENGTH: 33
<212> TYPE: DNA
<213> ORGANISM: Artificial Sequence
<220> FEATURE:
<223> OTHER INFORMATION: Synthetic primer based on Aspergillus nidulans

<400> SEQUENCE: 20
tccccgcgga tggaagcttc gttaaggata att                               33

<210> SEQ ID NO 21
<211> LENGTH: 37
<212> TYPE: DNA
<213> ORGANISM: Artificial Sequence
<220> FEATURE:
<223> OTHER INFORMATION: Synthetic primer based on Aspergillus nidulans

<400> SEQUENCE: 21
ataagaatgc ggccgcctac cagattaggg agcatat                           37

<210> SEQ ID NO 22
<211> LENGTH: 2229
<212> TYPE: DNA
<213> ORGANISM: Aspergillus nidulans

<400> SEQUENCE: 22

| | | | | | |
|---|---|---|---|---|---|
| ccgcggatgg | aagcttcgtt | aaggataatt | gcctcttttc | gaacacctat tcatgttgat | 60 |
| tagcgatcat | tagttatccg | gctcggtaac | agaactatgg | catactgaac gtcaacttcg | 120 |
| gaacacgggt | ctctcctagt | tccggatgga | ctaactgccc | gtcttccgag aacgtcagct | 180 |
| atataagtat | ctttccccct | tcaacgctat | cacgccatac | cttaaagaaa acgcgcagct | 240 |
| caagcattca | gatccacata | attaagctac | tgacgtgaac | tatcaaattc catccaccaa | 300 |
| ttgcccacga | tggtcgagat | ctccatcccc | gcaaactacg | gtacgtccg ccacggtgtt | 360 |
| accaaacatt | actagccagc | tagctcagtc | ttaccccggt | catgagacca ccccatgcta | 420 |
| atcatataac | gatctttatt | atagatatgc | catcgccgtt | tcgctaggcg caatccctgt | 480 |
| cctgggattc | atccatggtg | tcctcgtcgg | ctcttttcgc | aaggccgctg gcgtgccgta | 540 |
| cccccacgcc | tatgccagca | ttgagcaatg | taaagctaac | gtgcgtgagc caagaaact | 600 |
| aaatacctat | agcaaaacag | attgtgttcc | aagagagagt | actaaatgac gtttgtgaac | 660 |
| agcccaaagc | ctacaaattc | aactgcgcac | aacgcgccca | cggcaacttc ctcgagaacg | 720 |
| cgccgcagac | aatgctctct | atcctggtgg | caggcgtcaa | gtacccagag cagcagcgg | 780 |
| gcttaggagc | ggcctgggtt | gttctccgca | ccctctacat | gctgggctat atttatagcg | 840 |
| acaagccgaa | cggcaccggc | aggtacaatg | gttcgctgta | cttgcttgcg caagcgggtc | 900 |
| tttggggatt | gagcgcattt | ggtgttgcaa | aggatttgat | gtaaatgtag tcgacatctt | 960 |
| agcacagagg | ggagagttga | taaaatgtgg | tctgtttgaa | tgatagtcgg ttcgtgacc | 1020 |
| tatattcgtg | atagtggaga | taggtctgcg | cctatcttat | cgggccggag caaaaattcc | 1080 |
| accgcagcgg | ggtgagtttt | cgttatacag | ccatcccact | tccagcttca aattgtcagt | 1140 |
| ttaatccagc | ccaattcaat | cattggaaga | ccgccatcat | gtcttcgaag tcccacctcc | 1200 |
| cctacgcaat | tcgcgcaacc | aaccatccca | acccttaaac | atctaaactc ttctccatcg | 1260 |
| ccgaggagaa | gaaaaccaac | gtcaccgtct | ccgcagacgt | tactacttcc gccgagctcc | 1320 |
| tcgatcttgc | tgaccgtaca | tcctgcacca | atgcccctcc | aggataacaa atagctgatg | 1380 |
| cgtagtgagt | acaggcctag | gcccctatat | cgcagttctg | aaaacccaca tcgacatcct | 1440 |
| caccgatctc | accccgtcga | cccttttcctc | gctccaatcc | ctcgcgacaa agcacaactt | 1500 |
| cctcatcttt | gaggaccgca | agttcatcga | catcggcaac | accgtgcaaa agcagtacca | 1560 |
| cggtggcgct | ctccgcatct | ccgaatgggc | acacatcatc | aactgcgcca tcctgccggg | 1620 |
| cgaagggatc | gtcgaggccc | tcgcacagac | aaccaagtct | cctgacttta aagacgcgaa | 1680 |
| tcaacgaggt | ctcctgattc | ttgccgagat | gacgagtaag | ggatctcttg cgacagggga | 1740 |
| gtcacaggca | cgctcggttg | agtacgcgcg | gaagtataag | gggtttgtga tgggattcgt | 1800 |
| gagtacaagg | gcgttgagtg | aggtgctgcc | cgaacagaaa | gaggagagcg aggattttgt | 1860 |
| cgtctttacg | actggggtga | atctgtcgga | taagggggat | aagctggggc agcagtatca | 1920 |
| gacacctggg | tcgcggttg | ggcgaggtgc | ggactttatc | attgcgggta ggggcatcta | 1980 |
| taaggcggac | gatccagtcg | aggcggttca | gaggtaccgg | gaggaaggct ggaaagctta | 2040 |
| cgagaaaaga | gttggacttt | gagtgtgagt | ggaaatgtgt | aacggtattg actaaaaggg | 2100 |
| atccatatgt | ttattgcagc | cagcatagta | ttaccagaaa | gagcctcact gacggctcta | 2160 |

-continued

```
gtagtattcg aacagatatt attgtgacca gctctgaacg atatgctccc taatctggta      2220
ggcggccgc                                                              2229

<210> SEQ ID NO 23
<211> LENGTH: 30
<212> TYPE: DNA
<213> ORGANISM: Artificial Sequence
<220> FEATURE:
<223> OTHER INFORMATION: Synthetic primer based on Aspergillus nidulans

<400> SEQUENCE: 23
tgctctagag gcgccatggc cgaagaagcg                                         30

<210> SEQ ID NO 24
<211> LENGTH: 30
<212> TYPE: DNA
<213> ORGANISM: Artificial Sequence
<220> FEATURE:
<223> OTHER INFORMATION: Synthetic primer based on Aspergillus nidulans

<400> SEQUENCE: 24
tcccccgggg taaccagaag tcataccgtc                                         30
```

CHIMERIC PRE-ACTIVATED TRANSCRIPTION FACTORS

CROSS REFERENCE TO RELATED APPLICATIONS

This application claims benefit from provisional applications "Fungal Switching" (U.S. Ser. No. 60/066,129), "*Candida albicans* RIM1 Gene is Essential for Invasive Hyphal Growth" (U.S. Ser. No. 60/066,308), and "*Candida albicans* RIM1 Gene is Essential for Invasive Hyphal Growth" (U.S. Ser. No. 60/066,462), which were filed on Nov. 19, 1997, Nov. 21, 1997, and Nov. 24, 1997, respectively.

STATEMENT AS TO FEDERALLY SPONSORED RESEARCH

The invention was supported, in whole or in part, by funding from the Government. The Government has certain rights in the invention.

BACKGROUND OF THE INVENTION

Fungal species are the commercial source of many medicinally useful products, such as antibiotics (e.g., beta-lactam antibiotics such as penicillin, cephalosporin, and their derivatives), anti-hypercholesterolemic agents (e.g., lovastatin and compactin), immunosuppressives (e.g., cyclosporin), and antifungal drugs (e.g., pneumocandin and echinocandin). All of these drugs are fungal secondary metabolites, small secreted molecules that fungi utilize against competitors in their microbial environment. Fungi also produce commercially important enzymes (e.g., cellulases, proteases, and lipases) and other products (e.g., citric acid, gibberellic acid, natural pigments, and flavorings).

The production of secondary metabolites, enzymes, and other products is regulated by coordinated gene expression. For example, the production of penicillin is limited by the activity of two enzymes, encoded by the ipnA and acvA genes. PacC, a zinc-finger transcription factor, binds to sequences upstream of these two genes. Moreover, increased activity of PacC leads to both increased enzyme activity and penicillin production.

Our understanding of transcriptional regulation of secondary metabolite production, as exemplified above, has increased greatly over the past decade. To date, however, the use of genetically-engineered transcription factors has not been applied to increase production of commercially-important fungal products. In contrast, methods to increase production of penicillin currently rely upon mutagenesis and selection for mutants which display increased secondary metabolite production.

SUMMARY OF THE INVENTION

The invention provides a means to increase the production of secondary metabolites in fungi by genetic manipulation of the fungal organism itself. The ability to increase fungal secondary metabolite production has at least two important applications. First, it will allow increased production of existing secondary metabolites which are useful in clinical and experimental settings. Second, increasing production of secondary metabolites will facilitate identification of new compounds in fungi that otherwise make undetectable levels of these compounds in the laboratory.

Accordingly, in one aspect, the invention features a two-part chimeric transcription factor including (i) a pre-activated transcription factor functional in a fungal strain, and (ii) a transcription activation domain that is different from the transcription activation domain naturally associated with the transcription factor. In a preferred embodiment, the transcriptional activity of the chimeric transcription factor is greater than the transcriptional activity naturally associated with the pre-activated transcription factor. In another preferred embodiment, the pre-activated transcription factor is pre-activated by truncation. In a related preferred embodiment, the pre-activated transcription factor includes a substitution of a serine or threonine residue with an alanine, aspartic acid, or glutamic acid residue, wherein the substitution pre-activates the transcription factor (e.g., by mimicking or otherwise altering phosphorylation). In another preferred embodiment, the transcription factor is a member of the PacC family (defined below) and can be pre-activated. In a related preferred embodiment, the pre-activated transcription factor contains portions of the amino acid sequence shown in FIG. 1 (SEQ ID NOs: 1–6).

In another aspect, the invention features a vector including DNA encoding a chimeric transcription factor including (i) a pre-activated transcription factor functional in a fungal strain, and (ii) a transcription activation domain that is different from the transcription activation domain naturally associated with the transcription factor. The DNA is operably linked to a promoter capable of directing and regulating expression of the chimeric transcription factor in a fungal strain.

The transcription factor encoded within the vector described above is expressed in a fungal cell, such as a filamentous fungal cell, which produces the secondary metabolite of interest and in which expression of the transcription factor increases the production of the secondary metabolite by the cell. The secondary metabolite can be non-proteinaceous or it can be a protein or peptide.

In another aspect, the invention features a method of producing a secondary metabolite of interest, including the steps of (i) introducing into a fungal cell, such as a filamentous fungal cell, a vector including a promoter capable of controlling gene expression in the fungal cell, and a nucleic acid encoding a two-part transcription factor including a DNA-binding domain and a transcription activation domain; and (ii) culturing the fungal cell under secondary metabolite-producing conditions. In a preferred embodiment, the transcription activation domain is different from the transcription activation domain naturally associated with the DNA-binding domain. In other preferred embodiments, the transcription factor is a pre-activated transcription factor (pre-activated by substitution of a serine or threonine residue with an alanine, aspartic acid, or glutamic acid residue, or pre-activated by truncation). In other preferred embodiments, the DNA binding domain of the transcription factor is from a fungal transcriptional activator or from a fungal transcriptional repressor.

By "pre-activated transcription factor" is meant a transcription factor or fragment thereof that, compared to the precursor molecule, is capable of 1) increased binding, either direct or indirect, to a specific DNA sequence located in a gene regulatory region (e.g., a promoter), or 2) increased transcription activating properties. Pre-activated transcription factors may be able to activate transcription from promoters, but this is not necessarily the case. For example, a transcription factor DNA-binding domain with binding properties but no transactivation activity is considered to be a pre-activated transcription factor. "Pre-activation by truncation" or "pre-activated by truncation" means that removal of a portion of the protein leads to pre-activation. This occurs in vivo through proteolytic cleavage. In the invention, pre-activation by truncation is achieved with the use of DNA that encodes a pre-activated form of the protein, excluding portions of the protein that would be proteolytically cleaved in vivo.

By "substantially identical" is meant a polypeptide or nucleic acid exhibiting at least 50%, preferably 85%, more preferably 90%, and most preferably 95% identity to a reference amino acid or nucleic acid sequence. For polypeptides, the length of comparison sequences will generally be at least 16 amino acids, preferably at least 20 amino acids, more preferably at least 25 amino acids, and most preferably 35 amino acids. For nucleic acids, the length of comparison sequences will generally be at least 50 nucleotides, preferably at least 60 nucleotides, more preferably at least 75 nucleotides, and most preferably 110 nucleotides.

By "promoter" is meant a sequence sufficient to direct and/or regulate transcription. Also included in the invention are those elements which are sufficient to render promoter-dependent gene expression controllable for cell type-specific, tissue-specific, temporal-specific, or inducible by external signals or agents; such elements may be located in the 5' or 3' or intron sequence regions of the native gene.

By "operably linked" is meant that a gene and one or more regulatory sequences are connected in such a way as to permit gene expression when the appropriate molecules (e.g., transcriptional activator proteins) are bound to the regulatory sequences.

Other features and advantages of the invention will be apparent from the following description of the preferred embodiments thereof, and from the claims.

DRAWING

FIG. 1 is an alignment of the zinc-finger DNA-binding domain of PacC family members from *Aspergillus nidulans* (SEQ ID NO: 1), *Aspergillus niger* (SEQ ID NO: 2), *Penicillium chrysogenum* (SEQ ID NO: 3), *Yarrowia lipolytica* (SEQ ID NO: 4), *Candida albicans* (SEQ ID NO: 5), and *Saccharomyces cerevisiae* (SEQ ID NO: 6). Identity is represented by shaded regions; similarity is represented by boxed regions.

DETAILED DESCRIPTION

The invention features a two-part chimeric protein including a pre-activated transcription factor and a strong transcription activation domain for regulating fungal gene expression. The protein is encoded by nucleic acids operably linked to a strong promoter in a vector which allows for expression in fungal cells. The effect of the transcription factor is to facilitate expression of a protein which itself is a desired product, or which acts as an element (e.g., an enzyme) by which a desired product is made by the host fungal cell. Each of these components is described below. Experimental examples described herein are intended to illustrate, not limit, the scope of the claimed invention.

Pre-Activated Transcription Factor

The vectors of the invention can include DNA encoding any proteinaceous transcription factor that can be provided in pre-activated form; i.e., the vector encodes the protein in a form in which it is already activated; i.e., no post-translational processing is required for the protein to be active in a fungal cell to bind to regulatory DNA of the cell to facilitate gene expression.

Transcription factors regulate the level of gene expression by affecting the activity of the core transcriptional machinery at the promoter of each gene. Several mechanisms have evolved to control the activity of transcription factors.

Post-translational modification is one mechanism by which transcription factors are regulated. Proteolytic cleavage is one post-translational mechanism for regulating the activity of a transcription factor (e.g., Pahl and Baeuerle, *Curr. Opin. Cell Biol.*, 1996, 8:340–347; Goodbourn and King, *Biochem. Soc. Trans.*, 1997, 25:498–502; Fan and Maniatis, *Nature*, 1991, 354:395–398). The fungal PacC family of transcription factors is one class of proteins that can be activated by proteolysis. Activating mutations have been described for PacC family members (see below); these mutations truncate the encoded protein, resulting in the production of a pre-activated form of the transcription factor.

Another method for pre-activating a transcription factor is to mimic the modifications which normally regulate its activity. For example, phosphorylation has been shown to positively regulate the activity of some transcription factors and negatively regulate that of others (see review by Hunter and Karin, *Cell*, 1992, 70:375–387). Other forms of post-translational modifications that can increase the activity of transcription factors include acetylation (Gu and Roeder, *Cell*, 1997, 90:595–606) and alkylation (e.g., methylation) (Chinenov et al., *J. Biol. Chem.*, 1998, 273:6203–6209; Sakashita et al., *J Biochem* (Tokyo), 1995, 118:1184–1191).

Dephosphorylation of particular residues can increase the activity of many transcription factors. Phosphorylation most commonly occurs on serine (Ser), threonine (Thr), and tyrosine (Tyr) residues; in some instance residues such as aspartate (Asp) and histidine (His) can be phosphorylated. The coding sequence for the phosphorylated residue can be mutated to encode an amino acid that cannot be phosphorylated and does not have a negatively charged side chain (e.g., alanine (Ala)). Ser→GAla, Thr→Ala, Tyr→Ala, and Asp→Ala substitutions are frequently used in the art to produce a pre-activated transcription factor (see, for example, Chen et al., *Proc. Natl. Acad. Sci. U.S.A.*, 1998, 95:2349–2354; Song et al., *Mol. Cell Biol.*, 1998, 18:4994–4999; O'Reilly et al., *EMBO J.*, 1997, 16:2420–2430; Hao et al., *J. Biol. Chem.*, 1996, 271:29380–29385).

Phosphorylation can also increase the activity of a transcription factor. Mutations of Glu or Asp for Ser, Thr, or Tyr are frequently used in the art to mimic a phosphorylation event and pre-activate a transcription factor (see, for example, Hoeffler et al., *Nucleic Acids Res.*, 1994, 22:1305–12; Hao et al., supra). Mutations that result in a substitution of Glu for Asp, at Asp residues which can be phosphorylated, can also cause activation (Klose et al., *J. Mol. Biol.*, 1993, 232:67–78; Krems et al., *Curr. Genet.*, 1996, 29:327–34; Nohaile et al., *J. Mol. Biol.*, 1997, 273:299–316).

Other mutations can be made that mimic activating post-translational modifications. For example, the *E. coli* Ada transcription factor is activated by methylation of cysteine (Cys) residue 69. A Cys→His substitution was found to result in activation (Taketomi et al., *Mol. Gen. Genet.*, 1996, 250:523–532). This particular substitution was identified by substituting Cys 69 with each of the other nineteen amino acids. Alternatively, in instances where no obvious substitution can be made to mimic a modification (e.g., acetylation), a random mutagenesis is performed to identify constitutively active forms of transcription factors (see, for example, Onishi et al., *Mol. Cell Biol.*, 1998, 18:3871–3879). This technique can employ simple and rapid phenotypic or reporter selections, such as those described herein, to identify activated forms. For example, a *Saccha-*

*romyces cerevisiae* strain containing a reporter construct can be used to select for activated forms Specifically, the ipnA promoter ($P_{ipnA}$) from *Aspergillus nidulans* may be fused to a gene from *Saccharomyces cerevisiae* that confers a growth advantage, such as HIS3, when PacC is pre-activated by a mutation. A $P_{ipnA}$-HIS$^3$ fusion has the added advantage that expression levels can be titrated by the compound 3-aminotriazole (3-AT). 3-AT is a competitive inhibitor of His3 that, when present in sufficient amounts, will inhibit the His3 expressed from $P_{ipnA}$ and prevent this strain from growing on SC-HIS. In this example, pacC coding sequence can be randomly mutagenized and vectors containing the mutated alleles are transformed into the reporter strain. Growth of a strain containing $P_{ipnA}$-HIS3 only occurs on SC-HIS+3-AT plates when $P_{ipnA}$-HIS3 expression is increased to overcome the competitive inhibition of His3 by 3-AT. This method provides a rapid technique for screening for mutations which pre-activate a transcription factor.

The PacC Family of Transcription Factors

One group of transcription factors useful in the invention are members of the PacC family. The PacC transcription factors regulate gene expression in response to changes in ambient pH. Members of the family have the following characteristics: 1) They display significant (at least 35%) amino acid sequence identity to the *Aspergillus nidulans* PacC protein (Tilbum et al., *EMBO J.*, 1995, 14:779–790). Such proteins have been identified in *Yarrowia lipolytica* (YlRim101p; Lambert et al., *Mol. Cell. Biol.*, 1997, 17:3966–3976), *Penicillium chrysogenum* (Suarez and Penalva, *Mol. Microbiol.*, 1996, 20:529–540), *Aspergillus niger* (MacCabe et al., *Mol. Gen. Genet.*, 1996, 250:367–374), *Saccharomyces cerevisiae* (Inv8/Rim101/Rim1; Su and Mitchell, *Nucleic Acids Res.*, 1993, 21:3789–3797), and *Candida albicans* (U.S. Ser. No. 09/189,462)(Table 1). 2) They contain a predicted DNA-binding region that includes three zinc fingers of the $Cys_2His_2$ class.

In addition, several PacC family member either have been shown to directly bind to or regulate expression of genes that contain a 5'-GCCAAG-3' or 5'-GCCAGG-3' element in upstream regulatory sequence (Tilbum et al., supra; Suarez and Penalva, supra). Furthermore, with the exception of PacC from *P. chrysogenum*, mutations that truncate the protein have either been identified or constructed, and these mutations result in activation of gene expression by the PacC family of proteins, even at low ambient pH (Tilbum et al., supra; van den Hombergh et al., *Mol. Gen. Genet.*, 1996, 251:542–550; Lambert et al., supra; Li and Mitchell, *Genetics*, 1997, 145:63–73). Finally, in both *A. nidulans* and *S. cerevisiae*, it has been demonstrated that specific proteolytic cleavage results in activation of signaling in vivo (Orejas et al., *Genes Dev.*, 1995, 9:1622–32; Li and Mitchell, supra).

Transcription Activation Domains

Transcription activation domains (TADs) are discrete regions of proteins which promote gene expression by a variety of mechanisms that ultimately result in the activation of RNA polymerase. A TAD generally is defined as the minimal motif that activates transcription when fused to a DNA-binding domain (DBD) (Webster et al., *Cell*, 1988, 52:169–178; Fischer et al., *Nature*, 1988, 332:853–856; Hope et al., *Nature*, 1988, 333:635–640). The invention can employ any TAD that can transactivate expression from a fungal gene promoter when the TAD is fused to an appropriate DBD. TADs are classified based on similarities in protein sequence and/or composition properties. These classes include the acidic-rich (e.g., Gal4, Gcn4, VP16, and Jun; Webster et al., supra; Fischer et al., supra; Hope et al., supra; Cress and Triezenberg, *Science*, 1991, 251:87–90; Struhl, *Nature*, 1988, 332:649–650), glutamine-rich (Sp1, Oct1, and Oct2; Courey and Tjian, *Cell*, 1988, 55:887–898; Tanaka et al., Mol. Cell Biol., 1994, 14:6046–6055; Tanaka and Herr, *Mol. Cell Biol.*, 1994, 14:6056–6067), and proline-rich TADs (CTF, NF-I, and EKLF; Mermod et al., *Cell*, 1989, 58:741–753; Tanese et al., *Genes Dev.*, 1991, 5:2212–2224; Chen and Bieker, *EMBO J.*, 1996, 15:5888–5896). Any of these classes of TADs may be used in the present invention. The ability of any particular TAD to transactivate from a particular promoter can be determined using simple, known selection screens.

It is also possible to artificially create either a TAD or a site-specific DBD. In one example, protein sequences which transactivate a reporter gene from a promoter of interest are selected from an expression library. In another example, protein sequences which specifically bind particular DNA sequences are selected. In each case, these sequences can then be mutated in a reiterative process to obtain either the optimal TAD sequence for the particular promoter, or the optimal DBD sequence for a particular DNA sequence. Transcription factors containing artificial elements produced by this or any other method are useful in the invention.

In the chimeric transcription factor of the featured invention, TADs may be used alone or in combination. For example, Sp1 contains multiple glutamine-rich TADs, and these domains act synergistically to promote gene expression (Courey and Tjian, supra; Courey et al., *Cell*, 1989, 59:827–836). Oct-2 contains both glutamine-rich and proline-rich TADs, and both are required for maximal expression when fused to either the Oct-2 or a heterologous DBD (Tanaka et al., supra). Thus, the use of two or more classes of TADs in one construct may amplify the induction of expression. Furthermore, homopolymeric stretches of proline or glutamine function as TADs (Gerber et al., *Science*, 1994, 263:808–811). In one example, a strong transcription factor has been created by fusion of the Gal4 DBD to a homopolymeric glutamine stretch linked to reiterated VP16 TADs (Schwechheimer et al., *Plant Mol. Biol.*, 1998, 36:195–204).

Fungal Promoters

The chimeric, pre-activated transcription factor is operably linked to a strong promoter, allowing for expression of the transcription factor in a fungal cell. Expression systems utilizing a wide variety of promoters in many fungi are known, including, but not limited to, *Aspergillus nidulans* (gpd: Punt et al., *Gene*, 1987, 56:117–124; Hunter et al., *Curr. Genet.*, 1992, 22:377–383; Glumoffet al., *Gene*, 1989, 84:311–318. alcA; Femandez-Abalos et al., *Mol. Microbiol.*, 1998, 27:121–130. glaa: Carrez et al., *Gene*, 1990, 94:147–154. amdS: Turnbull et al., *Appl. Environ. Microbiol.*, 1990, 56:2847–2852), *Aspergillus niger* (gpd: Punt et al., supra; Hunter et al., supra; Glumoff et al., supra. glaA: Tang et al., Chin. J. Biotechnol., 1996, 12:131–136. amdS promoter: Turnbull et al., supra), *Pichia pastoris* (alcohol oxidase I promoter: Payne et al., *Gene*, 1988, 62:127–134), *Pleurotus ostreatus* (*Lentinus edodes ras* promoter: Yanai et al., *Biosci. Biotechnol. Biochem.*, 1996, 60:472–475), *Phytophthora infestans* (Bremia lactucae Hsp70: Judelson et al., *Mol. Plant Microbe Interact.*, 1991, 4:602–607), *Neurospora crassa* (his3 promoter: Avalos et al., *Curr. Genet.*, 1989, 16:369–372), *Yarrowia lipolytica* (XPR2 promoter: Nicaud et al., *Curr. Genet.*, 1989, 16:253–260. TEF: Muller et al., Yeast, 1998, 14:1267–1283.), *Penicillium chrysogenum* (phoA promoter: Graessle et al., *Appl. Environ. Microbiol.*, 1997, 63:753–756), *Rhizopus delemar* (pyr4 promoter: Horiuchi et al., *Curr. Genet.*, 1995, 27:472–478), *Gliocladium virens* (prom1: Dave et al., *Appl. Microbiol Biotechnol.*, 1994, 41:352–358), and *Cochliobolus heterostrophus* (Monke and Shafer, *Mol. Gen. Genet.*, 1993, 241:73–80).

There are also simple techniques for isolating promoters in organisms with relatively unstudied genetics. One of these is a system based on selection of sequences with promoter activity (see, for example, Turgeon et al., *Mol. Cell Biol.*, 1987, 7:3297–3305; Weltring, *Curr. Genet.*, 1995, 28:190–196). This approach provides an easy method for isolating promoter fragments from a wide variety of fungi.

The constructs of the invention also preferably include a terminator sequence located 3' to the chimeric transcription factor coding sequence. Terminator sequences which function in numerous fungi are known in the art. These include those from *Aspergillus nidulans* trpC (Punt et al., supra; Hunter et al., supra; Glumoff et al., supra), *Lentinus edodes* priA (Yanai et al., supra), *Bremia lactucae* Ham34 (Judelson et al., supra), and *Aspergillus nidulans* argB (Carrez et al., supra).

Construction of Chimeric Transcription Factors

The pre-activated transcription factors of the invention display 1) increased binding, either direct or indirect, to a specific DNA sequence located in a gene regulatory region (e.g., a promoter) in vivo, and/or 2) increased transcription activating properties, relative to the precursor molecule. To this end, it is preferable that part or all of the DBD, the domain of the parental transcription factor which recognizes and binds to the DNA sequences, remain intact. Additional sequences from the parental transcription factor may also remain in the chimeric construct, or they may be removed. The TAD of the parental transcription factor may be removed, as the chimeric transcription factor will contain a TAD from another protein, such as the herpesvirus transactivator VP16, as described herein. The TAD from the parental transcription factor may also remain in the chimeric construct.

As described above, TADs can be acidic, glutamine-rich, or proline-rich. The ability of each of these TADs to function in any given fungal strain will vary. The acidic TADs have been shown to function in a wide variety of organisms, from *C. elegans* to humans, including fungi. Glutamine-rich and proline-rich TADs have also been shown to function in disparate organisms, including fungi. As described above, increased transactivation activity may be achieved by using multiple TADs from one category (Tanaka and Herr, supra). Furthermore, TADs from more than one class may be used in one chimeric protein (Schwechheimer et al., supra; Tanaka et al., supra). In the example described below, 4 VP16 TADs and a proline-rich TAD are placed in series.

The production of chimeric transcription factors which activate transcription is not limited to the use of parental transcription factors that themselves are transcriptional activators. Using this method, transcription factors which are transcriptional repressors may be converted to transcriptional activators by the addition of a TAD. An example is the *Saccharomyces cerevisiae* Mig1, which is a repressor of SUC2 expression. Deletion of mig1 derepresses SUC2 expression. A chimeric protein in which the DBD of Mig1 is fused to the VP16 TAD can activate transcription from promoters containing Mig1-binding sites and leads to increased expression of SUC2 (Ostling et al., *Mol Cell Biol.*, 1996, 16:753–61). Thus, the formation of a chimeric transcriptional activator may be performed for any transcription factor, whether it be an activator or a repressor.

The choice of parental transcription factor for use in the present invention depends upon the desired product one wishes to produce. The transcription factor must recognize a sequence in the promoter of a gene of interest. This gene may encode a protein which itself is a desired product, or one which acts as an element (e.g., an enzyme) in the pathway by which a desired product is made by the host fungal cell. For example, a chimeric transcription factor including PacC may be used if the desire is to increase the production of beta-lactam antibiotics. This is achieved by increasing the expression of at least two genes, ipnA and acvA, which encode enzymes in the penicillin production process.

One skilled in the art will recognize that there are standard techniques, including the ones described herein, which allow for rapid selection and screening of chimeric transcription factor constructs in order to ascertain which transcription factors are the strongest transcriptional activators.

Construction of Fungal Expression Vectors

To achieve high expression of the chimeric transcription factor, several types of expression vectors are known in the art (e.g., those described herein). The choice of expression vectors may depend on the type of fungus to be used. For example, expression of a chimeric transcription factor in *Aspergillus nidulans* may be achieved using the amdS promoter system (Turnbull et al., supra). The promoter element may be modified such that it also contains a DNA sequence recognized by the chimeric transcription factor. The expression of the chimeric transcription factor will induce increased activation from its own promoter, thus amplifying its own production. The expression vector may also include terminator sequences, as described above. For example, a suitable terminator for *Aspergillus nidulans* is the argB terminator.

The vector, once transformed into a fungal cell as described herein, may remain episomal, in which case the vector may also have an origin of replication. The vector may also integrate into the chromosomal DNA of the host cell. The expression of the integrated expression construct may depend on positional effects, and, thus, it may be necessary to screen through or select for transformants to isolate those with suitably high expression. Methods for screening and selection are described herein. The integrated expression construct may also alter the expression of endogenous genes of the fungal cell. This altered expression may be beneficial or detrimental to the survival of the cell or to the purpose of the production of the fungal cell. For example, if the purpose is to increase production of a beta-lactam antibiotic, then loss of expression of ipnA (which encodes isopenicillin N-synthase and is required for beta-lactam production) following integration of the expression construct would negate any benefits resulting from expression of the chimeric transcription factor. Thus, a secondary screen of transformants displaying characteristics suitably for the designed purpose may be performed. Methods for determining metabolite production are described herein.

In some cases, it may be beneficial to use a transcription factor which is not chimeric. Overexpression of a parental transcription factor may lead to an increase in secondary metabolites. This overexpressed protein may be constitutively active, due to overexpression or genetic mutation, or it may be regulated in a manner similar to the endogenous transcription factor. The fungal cell may be a wild-type strain, or it may contain one or more mutations (which may also increase production of secondary metabolites). Example mutations include those which result in duplication or rearrangement of biosynthetic genes (e.g., the penicillin gene cluster of ipnA, acvA, and aatA). Reporter genes, such as those described herein, or other exogenous genes may also be present in the fungal cells, either episomally or chromosomally.

Transformation

In order to introduce the construct into a fungal cell, one may utilize any of numerous transformation protocols (for review, see Punt and van den Hondel, *Methods Enzymol.*, 1992, 216:447–457; Timberlake and Marshall, *Science*, 1989, 244:1313–1317; Fincham, *Microbiol. Rev.*, 1989, 53:148–170). Suitable DNA transformation techniques include electroporation, polyethylene glycol-mediated, lithium acetate-mediated, and biolistic transformation (Brown et al., *Mol. Gen. Genet.*, 1998, 259:327–335; Zapanta et al., *Appl. Environ. Microbiol.*, 1998; 64:2624–2629; Thompson et al., *Yeast*, 1998, 14:565–571; Barreto et al., *FEMS Microbiol. Lett.*, 1997, 156:95–99; Nicolaisen and Geisen, *Microbiol. Res.*, 1996, 151:281–284; Wada et al., *Appl. Microbiol. Biotechnol.*, 1996, 45:652–657; Ozeki et al., *Biosci. Biotechnol. Biochem.*, 1994, 58:2224–2227; Lorito et al., *Curr. Genet.*, 1993, 24:349–356; Oda and Tonomura, *Curr. Genet.*, 1995, 27:131–134). If desired, one may target the DNA construct to a particular locus. Targeting homologous recombination techniques are currently practiced in many fungi, including, but not limited to, *Candida albicans* (Fonzi and Irwin, *Genetics*, 1993, 134: 717–728), *Ustilago maydis* (Fotheringham and Hollman, *Mol. Cell Biol.*, 1989, 9:4052–4055; Bolker et al., *Mol. Gen. Genet.*, 1995, 248:547–552), *Yarrowia lipolytica* (Neuveglise et al., *Gene* 1998, 213:37–46; Chen et al., *Appl. Microbiol. Biotechnol.*, 1997, 48:232–235; Cordero et al., *Appl. Microbiol. Biotechnol.*, 1996, 46:143–148), *Acremonium chrysogenum* (Skatrud et al., *Curr. Genet.*, 1987, 12:337–348; Walz and Kuck, *Curr. Genet.*, 1993, 24:421–427), *Magnaporthe grisea* (Sweigard et al., *Mol. Gen. Genet.*, 1992, 232:183–190); Kershaw et al., *EMBO J.*, 1998, 17:3838–3849), *Histoplasma capsulatum* (Woods et al., *J. Bacteriol.*, 1998, 180:5135–5143) and Aspergillus sp. (Miller et al., *Mol. Cell Biol.*, 1985, 5:1714–1721; de Ruiter-Jacobs et al., *Curr. Genet.*, 1989, 16:159–163; Gouka et al., *Curr. Genet.*, 1995, 27:536–540; van den Hombergh et al., *Mol. Gen. Genet.*, 1996, 251:542–550; D'Enfert, *Curr. Genet.*, 1996, 30:76–82; Weidner et al., *Curr. Genet.*, 1998, 33:378–385).

Methods for Selection and Screening Transformants

Reporter genes are useful for isolating transformants expressing functional chimeric transcription factors. The reporter genes may be operably linked to promoter sequence which is regulated by the chimeric transcription factor. Reporter genes include, but are not limited to, genes encoding β-galactosidase (lacZ), β-glucoronidase (GUS), β-glucosidase, and invertase, amino acid biosynthetic genes, e.g., the yeast LEU2, HIS3, LYS2, TRP1 genes (or homologous genes from other fungi, such as filamentous fungi, that encode proteins with the similar functional activities), nucleic acid biosynthetic genes, e.g., the yeast URA3 and ADE2 genes (or homologous genes from other fungi, such as filamentous fungi, that encode proteins with the similar functional activities), the mammalian chloramphenicol transacetylase (CAT) gene, or any surface antigen gene for which specific antibodies are available. A reporter gene may encode a protein detectable by luminescence or fluorescence, such as green fluorescent protein (GFP). Reporter genes may encode also any protein that provides a phenotypic marker, for example, a protein that is necessary for cell growth or viability, or a toxic protein leading to cell death, or the reporter gene may encode a protein detectable by a color assay leading to the presence or absence of color.

The choice of reporter gene will depend on the type of fungal cell to be transformed. It is preferable to have two reporter genes within the fungal cell. One reporter gene, when expressed, may provide a growth advantage to transformed cells which are expressing the chimeric transcription factor. This allows for isolation of such transformants though selective pressures. The other reporter gene may provide a colorimetric marker, such as the lacZ gene and its encoded protein, β-galactosidase. Alternatively, the second reporter may provide a fluorescent or luminescent marker, such as GFP. These reporters provide a method of quantifying expression levels from expression constructs comprising chimeric transcription factors. Screens and selections similar to the ones described may be used to optimize construction of chimeric transcription factors or expression constructs.

EXAMPLE

The following example describes a method for increasing the level of PacC activity over that caused by proteolysis or specific truncations. This invention may facilitate the increased production of fungal secondary metabolites including, but not limited to, penicillins and cephalosporins. Similar genetic engineering can be performed to alter the function of other transcription factors.

A construct that encodes a chimeric transcription factor is described below. In this example, a proline-rich TAD followed by multiple copies of the acidic-rich TAD from the herpes simplex virus VP16 protein are fused to a truncated, pre-activated PacC from *Aspergillus nidulans* (SEQ ID NO: 7). This construct may be integrated at the pyrG locus in *Aspergillus nidulans*, as described below. Expression of this chimeric polypeptide is regulated by the strong PGK promoter from *Aspergillus nidulans* and terminator sequences from the crnA gene of *Aspergillus nidulans*.

Several DNA cloning steps are required to create this chimeric construct. Bluescript KS (Stratagene, LaJolla, Calif.) is be used as a cloning vector. The primers 5'-aa ctgcagTAGTTGACCGTGTGATTGGGTTCT-3' (SEQ ID NO: 8)(lowercase letters denote sequences introduced for cloning and restriction sites are underlined) and 5'-ccg gaattcTTTGTAAACTGGCTTGAAGAT-3' (SEQ ID NO: 9) are used to amplify 347bp of crnA terminator sequence from genomic DNA template. The PCR product is PstI/EcoRI digested and then cloned into the KS polylinker to produce p1. Subsequently, complementary oligonucleotides 5' - gatccCCCCCCCCTCCTCCACCCCCACCCCCTCCC-3' (SEQ ID NO: 10) and 5'-GGGAGGGGGTGGGGGTGGAGGAGGGGGGGGg-3' (SEQ ID NO: 11) are annealed (this double-stranded oligonucleotide encodes a proline-rich motif) and the double-stranded product is ligated into SmaI/BamHI digested p1, yielding p2.

Next, the oligonucleotide primers 5'-cgc gatatcAAAGTCGCCCCCCCGACCGAT-3' (SEQ ID NO: 12) and 5'-cgcgatatcCCCACCGTACTCGTCAATTCC-3' (SEQ ID NO: 13) are used in PCR reactions to amplify a 258 bp fragment using pVP16 (Clontech, Palo Alto, Calif.) as template. This product encodes the acidic-rich domain of VP16. The product is digested with EcoRV, and ligation reaction is performed with >20 fold excess of EcoRV insert relative to SmaI-digested calf-alkaline phosphatase treated p2. Bacterial transformants are screened for plasmids that contain multiple tandem insertions of VP16 sequence. SmaI sites within the VP16 coding sequence allow for determination of the orientation of the insertion. Plasmids are selected that contain four insertions of the VP16 acidic-rich domain (p3). p3, then, encodes a proline-rich domain in-frame with four reiterations of the VP16 domain, and these TADs are linked to the crnA terminator.

In the next cloning step a truncated form of pacC is fused to the coding sequence for the TADs. Primers 5'-tgctctagaGGCGCCATGGCCGAAGAAGCG-3' (SEQ ID NO: 14) and 5'-cgcggatccGTAACCAGAAGTCATACCGTC-3' (SEQ ID NO: 15) are used to amplify a 1419 bp product (SEQ ID NO: 16) from an *Aspergillus nidulans* cDNA library. This product is XbaI/BamHI digested and ligated into digested p3 to produce p4. This cloning reaction introduces a form of pacC that lacks the carboxy-terminal 209 amino acids in-frame with the described TADs.

An additional cloning step is required in order to place the coding sequence for this chimera under the control of a strong promoter. Primers 5'-ataagaatgcggccgcCCTCTGCATTATTGTCTTATC-3' (SEQ ID NO: 17) and 5'-tgctctagaAGACATTGTTGCTATAGCTGT-3' (SEQ ID NO: 18) are used to amplify 689 bp of PGK promoter sequence (SEQ ID NO: 19) from *Aspergillus nidulans* genomic DNA. This fragment is NotI/XbaI digested and cloned into digested p4 in order to yield p5. Thus, p5 contains coding sequence for an 815 amino acid chimeric transcription factor to be expressed from the PGK promoter.

To decrease the extent of position effects, the p5 construct is targeted to the pyrG locus. Oligonucleotides 5'-tccccgcggATGGAAGCTTCGTTAAGGATAATT-3' (SEQ ID NO: 20) and 5'-ataagaatgcggccgcCTACCAGATTAGGGAGCATAT-3' (SEQ ID NO: 21) are used to amplify a 2240bp product (SEQ ID NO: 22) from *Aspergillus nidulans* genomic DNA; this product contains coding and regulatory sequence for the pyrG gene that encodes orotidine-5'-phosphate decarboxylase. The 2240bp fragment is SacII/NotI digested, and then cloned into p5 to produce p6; this fragment is also cloned into KS to yield p7 (a control construct, containing regulatory sequence for the pyrG gene, but no PGK promoter or transcription factor). p6 and p7 are vector that can complement uridine auxotrophy, allowing for selection, and target the chimeric transcription factor to the pyrG locus. In addition, primers 5'-tgctctagaGGCGCCATGGCCGAAGAAGCG-3 (SEQ ID NO: 23) and 5' tccccggggGTAACCAGAAGTCATACCGTC-3' (SEQ ID NO: 24) are used to amplify the truncated form of PacC from an *Aspergillus nidulans* cDNA library. This fragment can be cloned into XbaI/SmaI digested p6 to produce p8. p8 is a control construct, used to monitor the activity of pre-activated PacC expressed from the PGK promoter, independent of the presence of heterologous TADs.

PEG-CaCl$_2$ (or other methods, described herein) may be used to transform protoplasts of a uridine auxotroph carrying a pyrG mutation (Ballance and Turner, *Gene*, 1985, 36:321–331). p6, p7, and p8 plasmid DNA are used to transform to uridine prototrophy. PCR and Southern analysis are performed to confirm single-copy integration at pyrG.

Several methods may be employed to assess the activity of wild-type, pre-activated, and chimeric PacC-TAD factors. Samples of mycelia may be taken from parallel fermentation of strains containing p6, p7, and p8. Northern blot analysis may be performed on RNA prepared from extracts of these mycelia. Probes are prepared from coding sequence for the ipnA and acvA genes of *Aspergillus nidulans*. Reporter constructs are valuable tools for examining the level of PacC activation. For example, ipnA and acvA are divergently transcribed from a common regulatory sequence. One may use constructs (e.g., pAXB4A; Brakhage et al., supra) that contain ipnA-lacZ and acvA-uidA reporters within the same plasmid; this particular plasmid can be targeted to the argB locus to ensure integration at a specific genomic locus. A strain carrying both argB and pyrG mutations can be sequentially transformed with the pyrG and reporter vectors, and enzyme assays can be performed on extracts from mycelia (van Gorcom et al., *Gene*, 1985, 40:99–106; Pobjecky et al., *Mol. Gen. Genet.*, 1990, 220:314–316). In addition, bioassays can be done to determine whether chimeric transcription factors increase the production of fungal secondary metabolites such as penicillin. Supernatant fluid from fermentations can be centrifuged and applied to wells containing indicator organisms such as *Bacillus calidolactis* (Smith et al., *Mol. Gen. Genet.*, 1989, 216:492–497). The application of all of these methods will promote a rapid and quantitative analysis of the efficacy of chimeric transcription factors.

Enhancement of Secondary Metabolite Production

The constructs and methods described herein may be used to increase the yields of currently marketed pharmaceuticals whose production, in whole or in part, is dependent upon a fungal fermentation. For example, in *Aspergillus nidulans*, penicillin biosynthesis is catalyzed by three enzymes encoded by ipnA, acvA, and aatA. Two of these genes, ipnA and acvA, are regulated directly by PacC. For example, $P_{ipnA}$ contains at least three PacC binding sites (ipnA2, ipnA3, and ipnA4AB)(Espeso and Penalva, *J Biol. Chem.*, 1996, 271:28825–28830). Expression of a truncated form of PacC has been shown to increase both expression of ipnA and acvA as well as production of penicillin. Activation (i.e., proteolytoc cleavage) of PacC requires the proteins encoded by the palA, palB, palC, palF, palH, and palI genes. It is possible that increased expression of at least some of these genes would result in increased production of penicillin. In the example described herein, ipnA and acvA expression are targeted for increase by formation of a chimeric transcription factor including the DNA-binding domain of PacC and 4 VP16 acidic TADs and a proline-rich TAD. Using the methods of the invention, production of other secondary metabolites can also be increased.

Examples of marketed secondary metabolites whose yields during fermentation could be increased by the methods of the invention include, without limitation, cyclosporin, penicillin, cephalosporin, ergot alkaloids, lovastatin, mevastatin, and the biosynthetic intermediates thereof. In addition, such methods can also be used to increase the likelihood of identifying new secondary metabolites with medicinal or agricultural value by increasing the concentration of such metabolites (and hence, the likelihood of detection by chemical or bioassay) in a fermentation broth.

Production and Detection Methods for Fungal Secondary Metabolites

Methods for fermentation and production of beta-lactam antibiotics, statins, ergot alkaloids, cyclosporin, and other fungal metabolites are described in Masurekar (*Biotechnology*, 1992, 21: 241–301), and references therein. The detection of secondary metabolites is specific for each metabolite and well-known to those practiced in the art. General methods to assess production and integrity of compounds in fermentation broths include, but are not limited to, bioassays for antimicrobial activity, high-performance liquid chromatography (HPLC) analysis, nuclear magnetic resonance, thin-layer chromatography, and absorbance spectrometry. Purification of metabolites from a fermentation broth can include removal of fungal cells or hyphae by centrifugation or filtration, adjustment of pH and/or salt concentrations after fermentation (to enhance solubility and/or subsequent extraction efficiency), and extraction of broths with appropriate organic solvents.

What is claimed is:

1. An isolated nucleic acid molecule encoding a chimeric pre-activated transcription factor, wherein said transcription factor consists of a DNA binding domain of a fungal transcription factor and a heterologous transcription activation domain.

2. An isolated nucleic acid molecule encoding a chimeric pre-activated transcription factor, wherein said transcription factor comprises a DNA binding domain of a fungal transcription factor and a transcription activation domain from another protein.

3. The nucleic acid molecule of claim 2, wherein said transcription factor further comprises its native transactivation domain.

4. A vector comprising the nucleic acid molecule of claim 1.

5. A fungal host cell comprising the vector of claim 4.

6. The fungal host cell of claim 5, wherein said cell is filamentous.

7. The fungal host cell of claim 5, wherein said cell produces a secondary metabolite, wherein the production of said secondary metabolite is increased upon transformation with said vector.

8. The fungal host cell of claim 7, wherein said secondary metabolite is non-proteinaceous.

9. The fungal host cell of claim 7, wherein said secondary metabolite is proteinaceous.

10. The fungal host cell of claim 7, wherein said secondary metabolite is penicillin.

11. The nucleic acid molecule of claim 1, wherein the DNA binding domain of said transcription factor binds to 5'-GCCAAG-3' or 5'-GCCAGG-3'.

12. The nucleic acid molecule of claim 1, wherein said DNA binding domain is derived from PacC transcription factor, wherein said PacC transcription factor has the amino acid sequence set forth in SEQ ID NO: 1, SEQ ID NO: 2, SEQ ID NO: 3, SEQ ID NO: 4, SEQ ID NO: 5, SEQ ID NO: 6 or SEQ ID NO: 7.

13. The nucleic acid molecule of claim 12, wherein said PacC transcription factor has the amino acid sequence set forth in SEQ ID NO: 1.

14. The nucleic acid molecule of claim 12, wherein said PacC transcription factor has the amino acid sequence set forth in SEQ ID NO: 2.

15. The nucleic acid molecule of claim 12, wherein said PacC transcription factor has the amino acid sequence set forth in SEQ ID NO: 3.

16. The nucleic acid molecule of claim 12, wherein said PacC transcription factor has the amino acid sequence set forth in SEQ ID NO: 4.

17. The nucleic acid molecule of claim 12, wherein said PacC transcription factor has the amino acid sequence set forth in SEQ ID NO: 5.

18. The nucleic acid molecule of claim 12, wherein said PacC transcription factor has the amino acid sequence set forth in SEQ ID NO: 6.

19. The nucleic acid molecule of claim 12, wherein said PacC transcription factor has the amino acid sequence set forth in SEQ ID NO: 7.

20. A method for producing a secondary metabolite in fungal cells, said method comprising transforming a fungal host cell capable of expressing said secondary metabolite with the vector comprising the nucleic acid molecule of claim 1, wherein the production of the secondary metabolite is increased.

21. A vector comprising the nucleic acid molecule of claim 2.

22. A fungal host cell comprising the vector of claim 21.

23. The fungal host cell of claim 22, wherein said cell is filamentous.

24. The fungal host cell of claim 22, wherein said cell produces a secondary metabolite, wherein the production of said secondary metabolite is increased upon transformation with said vector.

25. The fungal host cell of claim 24, wherein said secondary metabolite is non-proteinaceous.

26. The fungal host cell of claim 24, wherein said secondary metabolite is proteinaceous.

27. The fungal host cell of claim 24, wherein said secondary metabolite is penicillin.

28. The nucleic acid molecule of claim 2, wherein the DNA binding domain of said transcription factor binds to 5'-GCCAAG-3' or 5'-GCCAGG-3'.

29. The nucleic acid molecule of claim 2, wherein said DNA binding domain is derived from PacC transcription factor, wherein said PacC transcription factor has the amino acid sequence set forth in SEQ ID NO: 1, SEQ ID NO: 2, SEQ ID NO: 3, SEQ ID NO: 4, SEQ ID NO: 5, SEQ ID NO: 6 or SEQ ID NO: 7.

30. The nucleic acid molecule of claim 29, wherein said PacC transcription factor has the amino acid sequence set forth in SEQ ID NO: 1.

31. The nucleic acid molecule of claim 29, wherein said PacC transcription factor has the amino acid sequence set forth in SEQ ID NO: 2.

32. The nucleic acid molecule of claim 29, wherein said PacC transcription factor has the amino acid sequence set forth in SEQ ID NO: 3.

33. The nucleic acid molecule of claim 29, wherein said PacC transcription factor has the amino acid sequence set forth in SEQ ID NO: 4.

34. The nucleic acid molecule of claim 29, wherein said PacC transcription factor has the amino acid sequence set forth in SEQ ID NO: 5.

35. The nucleic acid molecule of claim 29, wherein said PacC transcription factor has the amino acid sequence set forth in SEQ ID NO: 6.

36. The nucleic acid molecule of claim 29, wherein said PacC transcription factor has the amino acid sequence set forth in SEQ ID NO: 7.

37. A method for producing a secondary metabolite in fungal cells, said method comprising transforming a fungal host cell capable of expressing said secondary metabolite with the vector comprising the nucleic acid molecule of claim 2, wherein the production of the secondary metabolite is increased.

38. A vector comprising the nucleic acid molecule of claim 3.

39. A fungal host cell comprising the vector of claim 38.

40. The fungal host cell of claim 39, wherein said cell is filamentous.

41. The fungal host cell of claim 39, wherein said cell produces a secondary metabolite, wherein the production of said secondary metabolite is increased upon transformation with said vector.

42. The fungal host cell of claim 41, wherein said secondary metabolite is non-proteinaceous.

43. The fungal host cell of claim 41, wherein said secondary metabolite is proteinaceous.

44. The fungal host cell of claim 41, wherein said secondary metabolite is penicillin.

45. The nucleic acid molecule of claim 3, wherein the DNA binding domain of said transcription factor binds to 5'-GCCAAG-3' or 5'-GCCAGG-3'.

46. The nucleic acid molecule of claim 3, wherein said DNA binding domain is derived from PacC transcription factor, wherein said PacC transcription factor has the amino acid sequence set forth in SEQ ID NO: 1, SEQ ID NO: 2, SEQ ID NO: 3, SEQ ID NO: 4, SEQ ID NO: 5, SEQ ID NO: 6 or SEQ ID NO: 7.

47. The nucleic acid molecule of claim 46, wherein said PacC transcription factor has the amino acid sequence set forth in SEQ ID NO: 1.

48. The nucleic acid molecule of claim 46, wherein said PacC transcription factor has the amino acid sequence set forth in SEQ ID NO: 2.

49. The nucleic acid molecule of claim 46, wherein said PacC transcription factor has the amino acid sequence set forth in SEQ ID NO: 3.

50. The nucleic acid molecule of claim 46, wherein said PacC transcription factor has the amino acid sequence set forth in SEQ ID NO: 4.

51. The nucleic acid molecule of claim 46, wherein said PacC transcription factor has the amino acid sequence set forth in SEQ ID NO: 5.

52. The nucleic acid molecule of claim 46, wherein said PacC transcription factor has the amino acid sequence set forth in SEQ ID NO: 6.

53. The nucleic acid molecule of claim 46, wherein said PacC transcription factor has the amino acid sequence set forth in SEQ ID NO: 7.

54. A method for producing a secondary metabolite in fungal cells, said method comprising transforming a fungal host cell capable of expressing said secondary metabolite with the vector comprising the nucleic acid molecule of claim 3, wherein the production of the secondary metabolite is increased.

* * * * *

UNITED STATES PATENT AND TRADEMARK OFFICE
CERTIFICATE OF CORRECTION

PATENT NO.     : 6,500,636 B1
DATED           : December 31, 2002
INVENTOR(S)  : Peter Hecht, Kevin T. Madden and Gerald R. Fink It is certified that error appears in the above-identified patent and that said Letters Patent is hereby corrected as shown below:

<u>Title page,</u>
Item [56], References Cited, OTHER PUBLICATIONS,
"Brackhage et" reference, change "la." to -- al. --; and "tans-acting" to -- trans-acting --; and "Brackhage," reference, change "*Apergillu*" to -- *Apergillus* --; and change "mermod et al." to -- Mermod et al. --; and change "878" to -- 898 --; and "Orejas et al.," reference, change "19950." to -- 1995) --; and change reference, "Suarex et al.," to -- Suarez et   al. --; and change "pbcC" and replace with -- pcbB --; and "Tanese et al.," reference change "the" and replace with -- the --; insert the following reference  -- Tilburn et al., "The Aspergillus PacC zinc finger transcription factor mediates regulation of both acid- and alkaline-expressed genes by ambient pH" *EMBO J*. 14:779-790 (1995) --.

<u>Column 4,</u>
Line 34, delete "GAla" and replace with -- Ala --.

<u>Column 5,</u>
Line 6, delete "HIS$^3$" and replace with -- HIS3 --.
Lines 26, 41 and 46, delete "Tilbum" and replace with -- Tilburn --.
Line 35, before "(Table)" insert -- , filed November 10, 1998 --.
After line 37, insert Table 1 (page 10 of original specification).

<u>Column 6,</u>
Line 49, insert a space after "Glumoff".
Line 50, delete "Femandez" and replace with -- Fernandez --.
Line 51, delete "glaa" and replace with -- glaA --.

<u>Column 10,</u>
Line 49, delete the extra spacings.

<u>Column 11,</u>
Line 9, delete the space after "1419".

UNITED STATES PATENT AND TRADEMARK OFFICE
CERTIFICATE OF CORRECTION

PATENT NO.    : 6,500,636 B1
DATED         : December 31, 2002
INVENTOR(S)   : Peter Hecht, Kevin T. Madden and Gerald R. Fink It is certified that error appears in the above-identified patent and that said Letters Patent is hereby corrected as shown below:

<u>Column 11,</u>
Line 9, delete the space after "689".
Lines 30 and 43, delete the extra spacings.

Signed and Sealed this

Third Day of February, 2004

JON W. DUDAS
*Acting Director of the United States Patent and Trademark Office*